United States Patent
Cowley et al.

(10) Patent No.: US 11,096,930 B2
(45) Date of Patent: Aug. 24, 2021

(54) SUBSTITUTED IMIDAZOPYRIDINE COMPOUNDS AS INHIBITORS OF INDOLEAMINE 2,3-DIOXYGENASE AND/OR TRYPTOPHAN-2,3-DIOXYGENASE

(71) Applicant: IOMet Pharma Ltd., Scotland (GB)

(72) Inventors: Phillip M. Cowley, Edinburgh (GB); Meredeth Ann McGowan, Boston, MA (US); Thomas J. Brown, Edinburgh (GB); Yongxin Han, Needham, MA (US); Kun Liu, Needham, MA (US); Qinglin Pu, Needham, MA (US); Alan Wise, Scotland (GB); Hongjun Zhang, Boston, MA (US); Hua Zhou, Acton, MA (US)

(73) Assignees: Merck Sharp & Dohme Corp., Rahway, NJ (US); IOmet Pharma Ltd., Edinburgh (GB)

( * ) Notice: Subject to any disclaimer, the term of this patent is extended or adjusted under 35 U.S.C. 154(b) by 286 days.

(21) Appl. No.: 16/088,873

(22) PCT Filed: Apr. 24, 2017

(86) PCT No.: PCT/US2017/029042
§ 371 (c)(1),
(2) Date: Sep. 27, 2018

(87) PCT Pub. No.: WO2017/189386
PCT Pub. Date: Nov. 2, 2017

(65) Prior Publication Data
US 2020/0230117 A1 Jul. 23, 2020

Related U.S. Application Data

(60) Provisional application No. 62/329,579, filed on Apr. 29, 2016.

(51) Int. Cl.
*C07D 519/00* (2006.01)
*A61K 31/438* (2006.01)

(52) U.S. Cl.
CPC .......... *A61K 31/438* (2013.01); *C07D 519/00* (2013.01)

(58) Field of Classification Search
CPC ........................... A61K 31/438; C07D 519/00
USPC ........................................................ 514/318
See application file for complete search history.

(56) References Cited

U.S. PATENT DOCUMENTS

| 7,326,705 B2 | 2/2008 | Ahmad et al. |
| 2008/0234313 A1 | 9/2008 | Ramsbeck et al. |
| 2009/0325936 A1 | 12/2009 | Bilodeau et al. |
| 2015/0025058 A1 | 1/2015 | Deutsch et al. |

FOREIGN PATENT DOCUMENTS

| WO | 2014159248 A1 | 10/2014 | |
| WO | 2015082499 A2 | 6/2015 | |
| WO | 2015181532 A1 | 12/2015 | |
| WO | 2016026772 A1 | 2/2016 | |
| WO | WO-2016060941 A1 * | 4/2016 | ......... A61K 31/4375 |
| WO | 2016071293 A2 | 5/2016 | |
| WO | 2017007700 A1 | 1/2017 | |

OTHER PUBLICATIONS

Xiangli Chen et al IDO,TDO, and AHR overexpression is associated with poor outcome in diffuse large B-cell lymphoma patients in the rituximab era (Year: 2020).*
European Search Reported, application 17780165.9, dated Oct. 30, 2019, 8 pages.
Tojo, Shingo et al., Crystal Structures and Structure-Activity Relationships ofCrystal Structures and Structure-Activity Relationships of Imidazothiazole Derivatives as IDO1 InhibitorsImidazothiazole Derivatives as IDO1 Inhibitors, ACS Medicinal Chemistry Letters, 2014, 1119-1123, 5(10).
Xu, Yue-Yang et al., Advances in the development of IDO1 inhibitors, Chinese Journal of New Drugs, 2016, 425-432, 25(4).

* cited by examiner

*Primary Examiner* — Rita J Desai
(74) *Attorney, Agent, or Firm* — Yong Zhao; Anna L. Cocuzzo

(57) ABSTRACT

Disclosed herein are substituted imidazopyridine compounds of formula (I) which are inhibitors of indoleamine 2,3-dioxygenase (IDO) and/or tryptophan-2,3-dioxygenase (TDO) enzymes: (I). Also disclosed herein are uses of the compounds in the potential treatment or prevention of an IDO- and/or TDO-associated disease or disorder. Also disclosed herein are compositions comprising these compounds. Further disclosed herein are uses of the compositions in the potential treatment or prevention of an IDO- and/or TDO-associated disease or disorder.

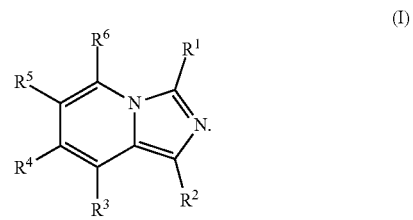

(I)

14 Claims, No Drawings

SUBSTITUTED IMIDAZOPYRIDINE COMPOUNDS AS INHIBITORS OF INDOLEAMINE 2,3-DIOXYGENASE AND/OR TRYPTOPHAN-2,3-DIOXYGENASE

CROSS-REFERENCE TO RELATED APPLICATIONS

The present application is 371 national phase application of international application no. PCT/US2017/029042, filed Apr. 24, 2017, which claims the benefit of U.S. Provisional Application No. 62/329,579, filed Apr. 29, 2016, hereby incorporated by reference in its entirety.

BACKGROUND OF THE INVENTION

The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN). The remaining 5% of tryptophan is metabolized by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to suppress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in Munn and Mellor, 2013).

The first step of tryptophan catabolism is catalyzed by either tryptophan-2,3-dioxygenase (TDO) or indoleamine-2,3-dioxygenase (IDO). Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

TDO is expressed at high levels in the liver and is responsible for regulating systemic tryptophan levels. TDO is not induced or regulated by signals from the immune system, however TDO expression can be induced by tryptophan or corticosteroids (Miller et al., 2004; Salter and Pogson, 1985). More recently, TDO has been found to be expressed in the brain, where it regulates the production of neuroactive tryptophan metabolites such as kynurenic acid and quinolinic acid (Kanai et al., 2009).

IDO is the predominant tryptophan catabolizing enzyme extra hepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumor-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternal-fetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyze the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007).

IDO-deficient mice are at a gross level phenotypical normal (Mellor et al., 2003), however, they are slightly more prone to induction of autoimmunity and stimulation of the innate immune system. IDO −/− knockout mice also display enhanced inflammatory-mediated colon carcinogenesis and exhibit resistance to inflammation-driven lung and skin cancers (Chang et al., 2011; Yan et al., 2010).

The TDO −/− knockout mouse appears phenotypically normal. However, the TDO knockout mice have a 9-fold increase in the plasma concentration of L-Trp, while IDO −/− knockout mice had WT levels of L-Trp, this suggests that TDO and not IDO regulates systemic Trp. TDO ablation increases Trp in the brain as well as serotonin (5-HT) and is therefore a modulator of anxiety related behavior (Kanai et al., 2009). TDO also plays a role in the maintenance of brain morphology in adult mice as TDO −/− mice show increased neurogenesis in the hippocampus and subventricular zone during adulthood (Funakoshi et al., 2011).

Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell anergy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated anergy by myeloid cells, including dendritic cells in tumor-draining lymph nodes (Munn et al., 2005).

Tryptophan metabolites such as kynurenine, kynurenic acid, 3-hydroxy-kynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Amt-Sim (PAS) family transcription factor. As kynurenine accumulates in a tumor, KYN binds the AHR, translocates to the nucleus and activates transcription of target genes regulated by dioxin-responsive elements (DREs). In T-helper-cells kynurenine results in the generation of regulatory T cells (Treg).

Pharmacological inhibitors of IDO and/or TDO have potential utility in a wide range of indications, including infectious diseases, cancer, neurological conditions and many other diseases.

SUMMARY OF THE INVENTION

Disclosed herein are novel compounds of formula (I) which are inhibitors of IDO and/or TDO enzymes. Also disclosed herein are uses of these compounds in the potential treatment or prevention of an IDO- and/or TDO-associated disease or disorder. Also disclosed herein are compositions comprising one or more of the compounds. Further disclosed herein are uses of these compositions in the potential prevention or treatment of an IDO- and/or TDO-associated disease or disorder.

DETAILED DESCRIPTION OF THE INVENTION

Compounds disclosed herein are IDO and/or TDO inhibitors. In one embodiment, disclosed herein is a compound of formula (I), or pharmaceutically acceptable salt thereof:

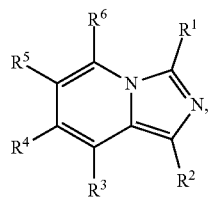

(I)

wherein:
each of $R^1$ and $R^2$ is independently selected from the group consisting of (1) H and (2) $NH_2$;
one of $R^3$ and $R^6$ is H and the other is $Y^1$;
each of $R^4$ and $R^5$ is independently selected from the group consisting of (1) H, (2) halogen, (3) $C_{1-6}$ alkyl, optionally substituted with one to three halogens, (4) $C_{3-6}$ cycloalkyl, (5) $C_{1-6}$ alkoxy, optionally substituted with one to three halogens, and (6) CN, and (7) $-NR^gR^{g'}$, each of $R^g$ and $R^{g'}$ is independently selected from the group consisting of H, $C_{1-6}$ alkyl, $-COH$, and $-COC_{1-6}$ alkyl;
$Y^1$ is a group having the following formula:

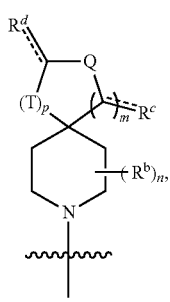

wherein
dashed line "------" represents an optional double bond;
Q is $-C(R^a)(R^{a'})-$, $-N(R^a)-$, or $-O-$;
T is $-C(R^a)(R^{a'})-$, $-N(R^a)-$, or $-O-$;
$R^a$ is selected from the group consisting of (1) H, (2) $C_{1-10}$ alkyl, (3) aryl, (4) $-C(O)-R^e$, (5) $-SO_2-NH_2$, and (6) $-SO_2-C_{1-4}$ alkyl; wherein each of the alkyl and aryl is optionally substituted with one to three substituents independently selected from halogen and heterocyclyl;
$R^{a'}$ is selected from the group consisting of (1) H and (2) $C_{1-6}$ alkyl;
$R^b$ is $C_{1-6}$ alkyl;
each of $R^c$ and $R^d$ is independently selected from the group consisting of (1) H, (2) $C_{1-6}$ alkyl and (3) oxo;
$R^e$ is selected from the group consisting of (1) $C_{1-6}$ alkyl, (2) aryl and (3) heteroaryl;
m is 0, 1 or 2;
n is 0, 1 or 2; and
p is 0 or 1.

In one embodiment of formula (I), each of $R^1$ and $R^2$ is H.

In one embodiment of formula (I), m is 1.

In one embodiment of formula (I), each of $R^4$ and $R^5$ is independently selected from the group consisting of (1) H, (2) halogen, (3) $C_{1-4}$ alkyl, optionally substituted with one to three halogens; and m is 1.

In one embodiment of formula (I), each of $R^4$ and $R^5$ is independently selected from the group consisting of (1) H, (2) halogen, (3) $C_{1-4}$ alkyl, optionally substituted with one to three halogens.

In one embodiment of formula (I), $R^3$ is H and $R^6$ is $Y^2$ having the following formula:

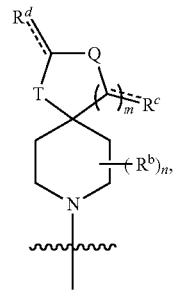

wherein
dashed line "------" represents an optional double bond;
Q is $-CH(R^a)-$ or $-N(R^a)-$;
T is $-CH_2-$ or $-NH-$;
$R^a$ is selected from the group consisting of (1) H, (2) $C_{1-6}$ alkyl, and (3) phenyl; wherein each of the alkyl and phenyl is optionally substituted with one to three substituents independently selected from halogen and a 5- or 6-membered hetero monocyclic group containing one hetero ring atom selected from oxygen, sulfur and nitrogen;
$R^b$ is $C_{1-4}$ alkyl;
each of $R^c$ and $R^d$ is independently H or oxo; and
m is 1.

In one embodiment of formula (I), $R^3$ is H and $R^6$ is $Y^3$ having the following formula:

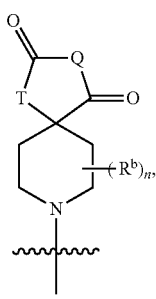

wherein

Q is —N(R$^a$)—;

T is —CH$_2$— or —NH—;

R$^a$ is selected from the group consisting of (1) H, (2) C$_{1-4}$ alkyl, optionally substituted with one to three substituents independently selected from halogen and a 5- or 6-membered hetero monocyclic group containing one oxygen ring atom, and (3) phenyl;

R$^b$ is methyl or ethyl; and n is 0, 1 or 2.

In one embodiment of formula (I), Y$^1$ is selected from the group consisting of:

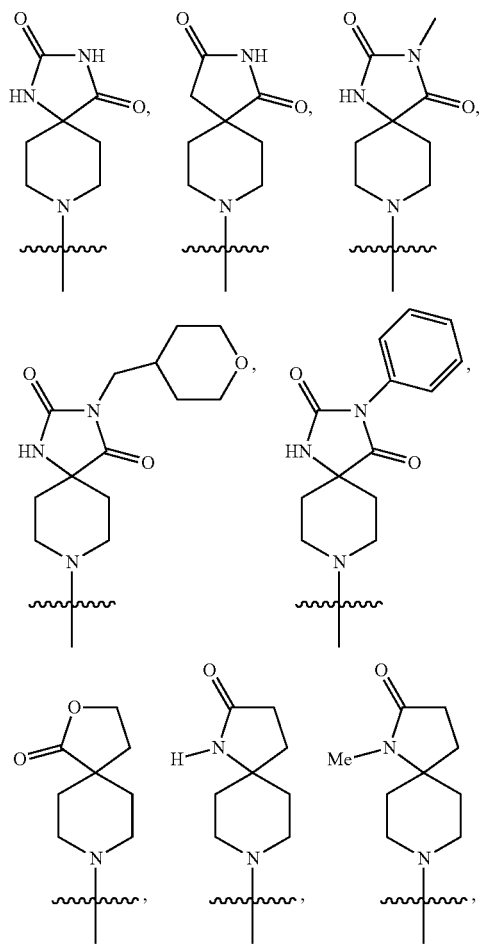

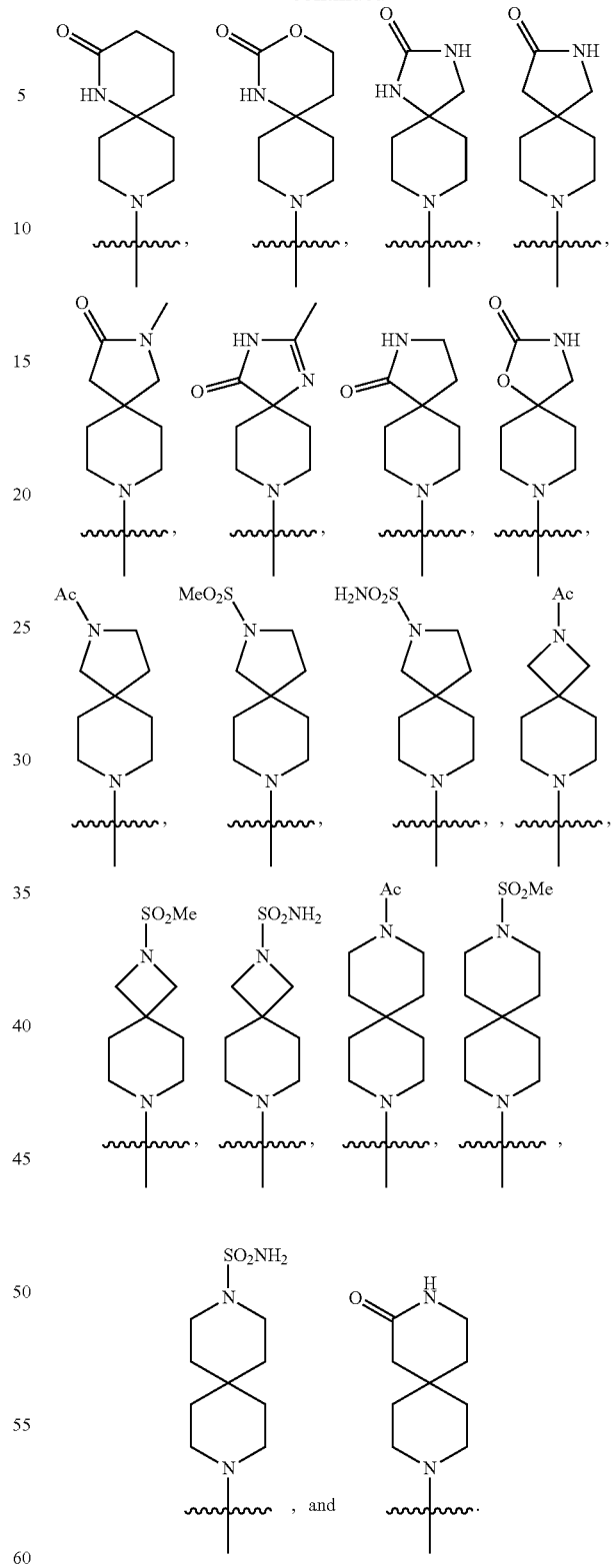

In one embodiment of formula (I), Y$^1$ is selected from the group consisting of:

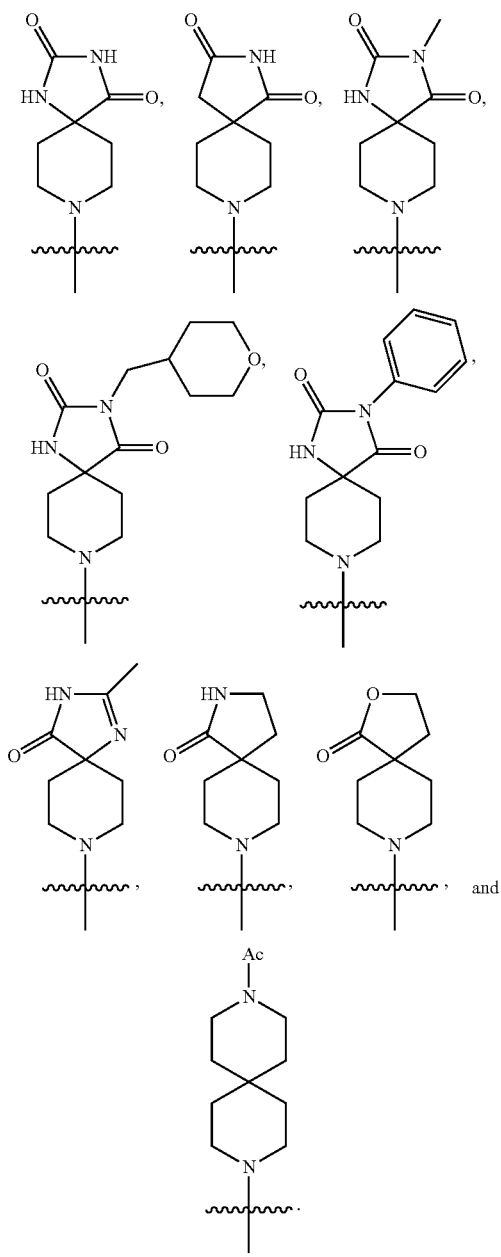

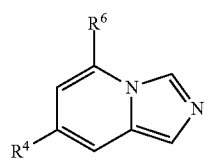

In one embodiment of formula (I), a compound is of formula I(a):

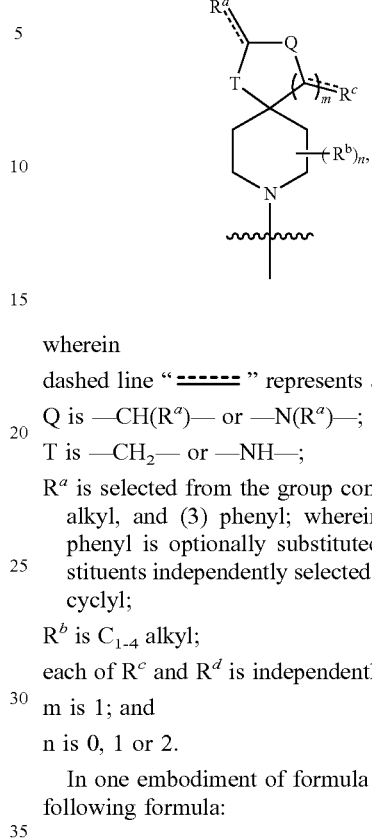

(Ia)

wherein:

$R^4$ is selected from the group consisting of (1) halogen and (2) $C_{1-4}$ alkyl, optionally substituted with one to three halogens;

$R^6$ is $Y^2$ having the following formula:

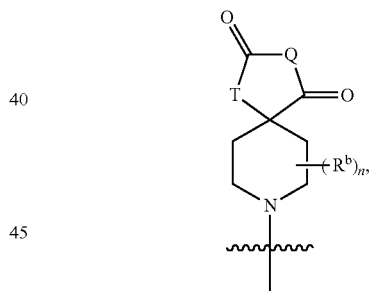

wherein dashed line "======" represents an optional double bond;

Q is —CH($R^a$)— or —N($R^a$)—;

T is —CH$_2$— or —NH—;

$R^a$ is selected from the group consisting of (1) H, (2) $C_{1-4}$ alkyl, and (3) phenyl; wherein each of the alkyl and phenyl is optionally substituted with one to three substituents independently selected from halogen and heterocyclyl;

$R^b$ is $C_{1-4}$ alkyl;

each of $R^c$ and $R^d$ is independently H or oxo;

m is 1; and n is 0, 1 or 2.

In one embodiment of formula (Ia), $R^6$ is $Y^3$ having the following formula:

wherein

Q is —N($R^a$)—;

T is —CH$_2$— or —NH—;

$R^a$ is selected from the group consisting of (1) H, (2) $C_{1-4}$ alkyl, optionally substituted with one to three substituents independently selected from halogen and a 5- or 6-membered hetero monocyclic group containing one oxygen ring atom, and (3) phenyl; and $R^b$ is methyl.

In one embodiment of formula (Ia), $R^a$ is selected from the group consisting of (1) H, (2) $C_{1-4}$ alkyl, optionally substituted with one to three substituents independently selected from halogen and tetrahydropyranyl, and (3) phenyl.

In one embodiment of formula (Ia), $Y^3$ is selected from the group consisting of:

[Chemical structures shown]

In one embodiment of formula (I), a compound is of formula I(b):

(Ib)

wherein
R$^5$ is selected from the group consisting of (1) halogen and (2) C$_{1-4}$ alkyl, optionally substituted with one to three halogens;

R$^3$ is Y$^2$ having the following formula:

[Chemical structure shown]

wherein
dashed line " ------ " represents an optional double bond;
Q is —CH(R$^a$)— or —N(R$^a$)—;
T is —CH$_2$— or —NH—;
R$^a$ is selected from the group consisting of (1) H, (2) C$_{1-6}$ alkyl, and (3) phenyl; wherein each of the alkyl and phenyl is optionally substituted with one to three substituents independently selected from halogen and heterocyclyl;
R$^b$ is C$_{1-4}$ alkyl;
each of R$^c$ and R$^d$ is independently H or oxo;
m is 1; and
n is 0, 1 or 2.

In one embodiment of formula (Ib), R$^3$ is Y$^3$ having the following formula:

[Chemical structure shown]

wherein
Q is —N(R$^a$)—;
T is —CH$_2$— or —NH—;
R$^a$ is selected from the group consisting of (1) H, (2) C$_{1-4}$ alkyl, optionally substituted with one to three substituents independently selected from halogen and a 5- or 6-membered hetero monocyclic group containing one oxygen ring atom, and (3) phenyl; and
R$^b$ is methyl.

In one embodiment of formula (Ib), R$^a$ is selected from the group consisting of (1) H, (2) C$_{1-4}$ alkyl, optionally substituted with one to three substituents independently selected from halogen and tetrahydropyranyl, and (3) phenyl.

In one embodiment of formula (Ib), Y$^3$ is selected from the group consisting of:

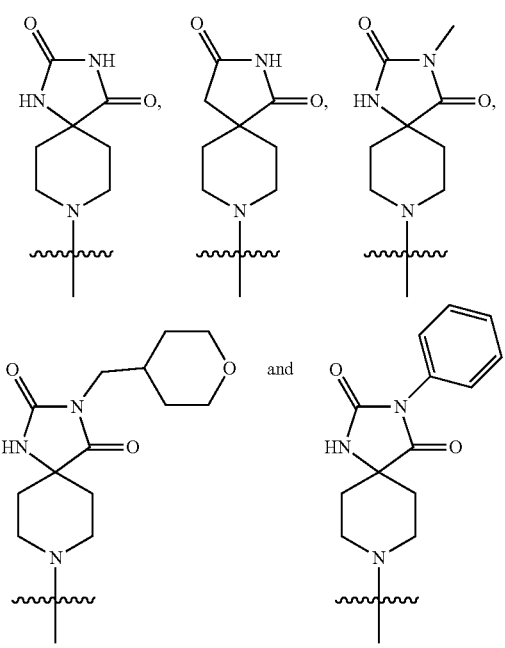

In one embodiment, a compound disclosed herein is selected from the group consisting of:
8-(7-(Trifluoromethyl)imidazo[1,5-a]pyridin-5-yl)-1,3,8-triazaspiro[4.5]decane-2,4-dione,
8-(7-bromoimidazo[1,5-a]pyridin-5-yl)-1,3,8-triazaspiro[4.5]decane-2,4-dione,
8-(7-chloroimidazo[1,5-a]pyridin-5-yl)-1,3,8-triazaspiro[4.5]decane-2,4-dione,
8-(6-(trifluoromethyl)imidazo[1,5-a]pyridin-8-yl)-1,3,8-triazaspiro[4.5]decane-2,4-dione,
6,6-dimethyl-8-(7-(trifluoromethyl)imidazo[1,5-a]pyridin-5-yl)-1,3,8-triazaspiro[4.5]decane-2,4-dione,
3-methyl-8-(7-(trifluoromethyl)imidazo[1,5-a]pyridin-5-yl)-1,3,8-triazaspiro[4.5]decane-2,4-dione,
3-((tetrahydro-2H-pyran-4-yl)methyl)-8-(7-(trifluoromethyl)imidazo[1,5-a]pyridin-5-yl)-1,3,8-triazaspiro[4.5]decane-2,4-dione,
8-(7-chloroimidazo[1,5-a]pyridin-5-yl)-6,6-dimethyl-1,3,8-triazaspiro[4.5]decane-2,4-dione,
3-phenyl-8-(7-(trifluoromethyl)imidazo[1,5-a]pyridin-5-yl)-1,3,8-triazaspiro[4.5]decane-2,4-dione,
3,6,6-trimethyl-8-(7-(trifluoromethyl)imidazo[1,5-a]pyridin-5-yl)-1,3,8-triazaspiro[4.5]decane-2,4-dione,
8-(7-chloroimidazo[1,5-a]pyridin-5-yl)-6,6-dimethyl-1,3,8-triazaspiro[4.5]decane-2,4-dione,
6,6-dimethyl-8-(6-(trifluoromethyl)imidazo[1,5-a]pyridin-8-yl)-1,3,8-triazaspiro[4.5]decane-2,4-dione,
8-(7-(trifluoromethyl)imidazo[1,5-a]pyridin-5-yl)-2,8-diazaspiro[4.5]decane-1,3-dione,
6,6-dimethyl-3-((tetrahydro-2H-pyran-4-yl)methyl)-8-(7-(trifluoromethyl)imidazo[1,5-a]pyridin-5-yl)-1,3,8-triazaspiro[4.5]decane-2,4-dione,
6,6-dimethyl-3-phenyl-8-(7-(trifluoromethyl)imidazo[1,5-a]pyridin-5-yl)-1,3,8-triazaspiro[4.5]decane-2,4-dione,
8-(7-bromoimidazo[1,5-a]pyridin-5-yl)-6,6-dimethyl-1,3,8-triazaspiro[4.5]decane-2,4-dione,
8-(7-(trifluoromethyl)imidazo[1,5-a]pyridin-5-yl)-2-oxa-8-azaspiro[4.5]decan-1-one,
2-methyl-8-(7-(trifluoromethyl)imidazo[1,5-a]pyridin-5-yl)-1,3,8-triazaspiro[4.5]dec-1-en-4-one,
1-(9-(7-(trifluoromethyl)imidazo[1,5-a]pyridin-5-yl)-3,9-diazaspiro[5.5]undecan-3-yl)ethan-1-one, and
8-(7-(trifluoromethyl)imidazo[1,5-a]pyridin-5-yl)-2,8-diazaspiro[4.5]decan-1-one;
or a pharmaceutically acceptable salt thereof.

Also disclosed herein is a composition comprising a compound of formula I, (Ia) or (Ib), and at least one pharmaceutically acceptable carrier.

Also disclosed herein is a method of inhibiting activity of an IDO enzyme comprising contacting the IDO with a compound of formula I, (Ia) or (Ib), or a pharmaceutically acceptable salt thereof.

Also disclosed herein is a method of inhibiting activity of a TDO enzyme comprising contacting the TDO with a compound of formula I, (Ia) or (Ib), or a pharmaceutically acceptable salt thereof.

Also disclosed herein is a method of inhibiting activity of both an IDO enzyme and a TDO enzyme comprising contacting the IDO and TDO with a compound of formula I, (Ia) or (Ib), or a pharmaceutically acceptable salt thereof.

Also disclosed herein is a method of inhibiting immunosuppression associated with an IDO and/or TDO activities in a patient comprising administering to said patient an effective amount of a compound of formula I, (Ia) or (Ib), or a pharmaceutically acceptable salt thereof.

Also disclosed herein is a potential method of treating cancer, viral infection, depression, a neurodegenerative disorder, trauma, age-related cataracts, organ transplant rejection, or an autoimmune disease in a patient comprising administering to said patient an effective amount of a compound of formula I, (Ia) or (Ib), or a pharmaceutically acceptable salt thereof.

Also disclosed herein is a potential method of treating melanoma in a patient comprising administering to said patient an effective amount of a compound of formula I, (Ia) or (Ib), or a pharmaceutically acceptable salt thereof.

Further disclosed herein is a compound of formula I, (Ia) or (Ib), or a pharmaceutically acceptable salt thereof, for use in therapy. In one embodiment, disclosed herein is the use of a compound of formula I, (Ia) or (Ib), or a pharmaceutically acceptable salt thereof, for the preparation of a medicament for use in therapy.

As used herein, "alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Cycloalkyl" refers to a monocyclic saturated carbocyclic ring having the specified number of carbon atoms. For example, $C_{3-7}$ cycloalkyl refers to a cycloalkyl group as defined herein having 3 to 7 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl. In one embodiment, a saturated 4-7 membered monocyclic heterocyclyl is azetidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I), (Ia) or (Ib), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I), (Ia) or (Ib).

Optical Isomers—Diastereomers—Geometric Isomers—Tautomers

Included herein are various isomers of the compounds of formula (I), (Ia) or (Ib). The term "isomers" refers to compounds that have the same composition and molecular weight but differ in physical and/or chemical properties. The structural difference may be in constitution (geometric isomers) or in the ability to rotate the plane of polarized light (stereosiomers).

With regard to stereoisomers, a compound of formula (I), (Ia) or (Ib) may have one or more asymmetric carbon atom and may occur as a racemic mixture or as individual enantiomers or diastereomers. All such isomeric forms are included herein, including mixtures thereof. If a compound of formula (I), (Ia) or (Ib) contains a double bond, the substituent may be in the E or Z configuration. If a compound of formula (I), (Ia) or (Ib) contains a disubstituted cycloalkyl, the cycloalkyl substituent may have a cis- or trans-configuration.

Any asymmetric atom (e.g., carbon) of a compound of formula (I), (Ia) or (Ib) can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of formula (I), (Ia) or (Ib) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds of formula (I), (Ia) or (Ib) include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2$H (i.e., Deuterium or "D"), $^3$H, $^{11}$C, $^{13}$C, $^{14}$C, $^{13}$N, $^{15}$N, $^{15}$O, $^{17}$O, $^{18}$O $^{32}$P, $^{35}$S, $^{18}$F, $^{23}$, $^{125}$I and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}$C, $^{18}$F, $^{15}$O and $^{13}$N, may be particularly desirable for PET or SPECT studies.

Isotopically-labeled compounds of formula (I), (Ia) or (Ib) can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I), (Ia) or (Ib) is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

These compounds disclosed herein may be useful in the potential treatment or prevention of IDO- and/or TDO-associated diseases. In one embodiment, these compounds may potentially inhibit the activity of the IDO enzyme, TDO enzyme or both IDO and TDO enzymes.

For example, the compounds disclosed herein can potentially be used to inhibit the activity of IDO and/or TDO in cells or in an individual in need of modulation of the enzyme by administering an effective amount of a compound. Further disclosed herein are methods of inhibiting the degradation of tryptophan in a system containing cells expressing IDO and/or TDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO- and/or TDO-mediated immunosuppression in a patient by administering to the patient an effective amount of a compound or composition recited herein. IDO- and/or TDO-mediated immunosuppression has been associated with, for example, cancers, tumor growth, metastasis, viral infection, viral replication, etc.

Also disclosed herein are methods of potential treatment of diseases associated with activity or expression, including abnormal activity and/or overexpression, of IDO and/or TDO in an individual (e.g., patient) by administering to the individual in need of such treatment an effective amount or dose of a compound disclosed herein or a pharmaceutical composition thereof. Exemplary diseases include any disease, disorder or condition that may be directly or indirectly linked to expression or activity of the IDO and/or TDO enzyme, such as over expression or abnormal activity. An IDO- and/or TDO-associated disease can also include any disease, disorder or condition that may be prevented, ameliorated, or cured by modulating enzyme activity. Examples of IDO- and/or TDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO and/or TDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO and/or TDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO and/or TDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with IDO and/or TDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I), (Ia) or (Ib).

One embodiment of the present invention provides for a method of potentially treating a disease or disorder associated with IDO and/or TDO enzyme activity comprising administration of an effective amount of a compound of formula (I), (Ia) or (Ib) to a subject in need of treatment thereof. In one embodiment, the disease or disorder associated with an IDO and/or TDO enzyme is a cell proliferation disorder.

In one embodiment, disclosed herein is the use of a compound of formula (I), (Ia) or (Ib) in a therapy. The compound may be useful in a method of inhibiting IDO and/or TDO enzyme activity in a subject, such as a mammal in need of such inhibition, comprising administering an effective amount of the compound to the subject.

In one embodiment, disclosed herein is a pharmaceutical composition comprising a compound of formula (I), (Ia) or (Ib), or a pharmaceutically acceptable salt thereof, for use in potential treatment of a disorder or disease related to IDO and/or TDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I) or (Ia), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I) or (Ia), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I), (Ia) or (Ib). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), (Ia) or (Ib), or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I), (Ia) or (Ib) and one or more other active agent(s) together in the same pharmaceutical composition, or a compound of formula (I), (Ia) or (Ib) and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I), (Ia) or (Ib) and at least one other therapeutic agent as a combined preparation for simultaneous, separate or sequential use in therapy. In one embodiment, the therapy is the treatment of a disease or disorder associated with IDO and/or TDO enzyme activity.

In one embodiment, the invention provides a kit comprising two or more separate pharmaceutical compositions, at least one of which contains a compound of formula (I), (Ia) or (Ib). In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I), (Ia) or (Ib) for treating a disease or disorder associated with IDO and/or TDO enzyme activity, wherein the medicament is prepared for administration with another active agent. The invention also provides the use of another active agent for treating a disease or disorder associated with an IDO and/or TDO enzyme, wherein the medicament is administered with a compound of formula (I), (Ia) or (Ib).

The invention also provides the use of a compound of formula (I), (Ia) or (Ib) for treating a disease or disorder associated with IDO and/or TDO enzyme activity, wherein the patient has previously (e.g. within 24 hours) been treated with another active agent. The invention also provides the use of another therapeutic agent for treating a disease or disorder associated with IDO and/or TDO enzyme activity, wherein the patient has previously (e.g. within 24 hours) been treated with a compound of formula (I), (Ia) or (Ib). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL

The following examples are intended to be illustrative only and not limiting in any way. Abbreviations used are those conventional in the art or the following.

ACN acetonitrile
° C. degree Celsius
DCM dichloromethane
DIPEA di-isopropylethylamine
DMF N,N-dimethylformamide
DMSO dimethylsulfoxide
EtOAc ethyl acetate
EtOH ethanol
g gram(s)
h hour(s)
HPLC high pressure liquid chromatography
kg kilogram
L liter(s)
LC liquid chromatography
LCMS liquid chromatography and mass spectrometry
MeOH methanol
MS mass spectrometry
MTBE methyl tert-butyl ether
min minute(s)

mL milliliter(s)
m/z mass to charge ratio
nm nanometer
nM nanomolar
N normal
NMP N-methyl-2-pyrrolidone
NMR nuclear magnetic resonance
RT room temperature
sat. saturated
TFA trifluoroacetic acid
TLC thin layer chromatography The compounds of formula (I), (Ia) or (Ib) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The compounds described herein may be made from commercially available starting materials or synthesized using known organic, inorganic, and/or enzymatic processes.

$^1$H NMR spectra were obtained on a Bruker AVANCE 300 spectrometer at 300 MHz or a Bruker AVANCE 400 spectrometer at 400 MHz with tetramethylsilane used as an internal reference. Thin-layer chromatography (TLC) was performed using Whatman No. 4500-101 (Diamond No. MK6F silica-gel 60 Å) plates. Visualization of TLC plates was performed using UV light (254 nm). Mass spectra were obtained on a Finnigan LCQ-DUO spectrometer using electrospray ionization. HPLC analyses were performed on an Agilent 1100 Series instrument. Impurities are expressed as % AUC by HPLC and are non-validated.

EXAMPLES

Example 1: 8-(7-(Trifluoromethyl)imidazo[1,5-a]pyridin-5-yl)-2,8-diazaspiro[4.5]decane-1,3-dione

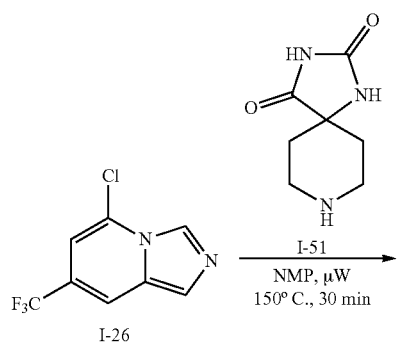

-continued

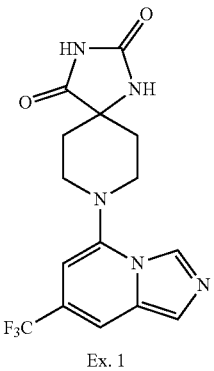
Ex. 1

Preparation of Ex. 1:
A solution of I-26 (80.0 mg, 0.36 mmol) and I-51 (60.0 mg, 0.36 mmol) in NMP (1.0 mL) was irradiated under microwave at 150° C. for 30 min. The reaction mixture was cooled to RT, diluted with EtOAc (20 mL) and washed with brine (3×20 mL). The organic layer was collected, dried over anhydrous Na$_2$SO$_4$ and concentrated under reduced pressure. The crude compound was purified by combiflash column chromatography using Redisep® column (12 g, 100% EtOAc) to afford Ex. 1 as a solid. MS (MM) m/z 354.1 [M+H]$^+$.
$^1$H NMR (300 MHz, DMSO-d$_6$): δ 10.77 (s, 1H), 8.58 (s, 1H), 8.47 (s, 1H), 7.89 (s, 1H), 7.72 (s, 1H), 6.25 (s, 1H), 3.40-3.24 (m, 2H), 3.12 (t, J=10.8 Hz, 2H), 2.21-2.13 (m, 2H), 1.77 (d, J=13.5 Hz, 2H).

Example 2: 8-(7-Bromoimidazo[1,5-a]pyridin-5-yl)-1,3,8-triazaspiro[4.5]decane-2,4-dione

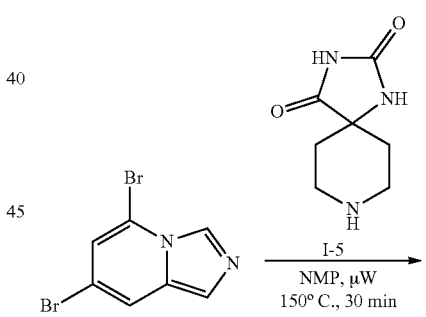

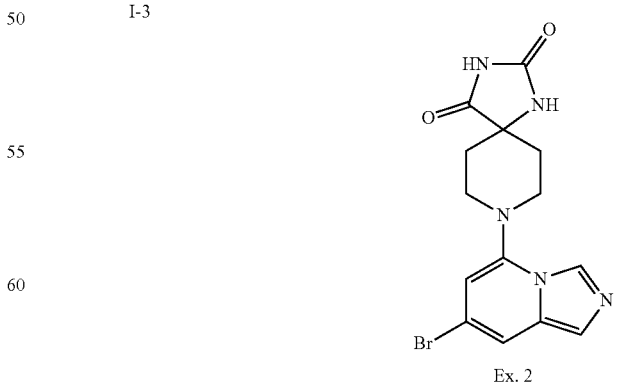
Ex. 2

A solution of compound I-3 (150 mg, 0.54 mmol) and compound I-5 (68.0 mg, 0.4 mmol) in NMP (1.0 mL) was irradiated under microwave for 30 min at 150° C. The reaction mixture was cooled to RT, loaded onto a Combiflash column and purified using Redisep® column (12 g, CH₂Cl₂/CH₃OH, 9:1) to afford the title compound as a solid. MS (MM) m/z 364.0 [M+H]⁺

$^1$H NMR (300 MHz, DMSO-d₆): δ 10.77 (s, 1H), 8.58 (s, 1H), 8.29 (s, 1H), 7.64 (s, 1H), 7.39 (s, 1H), 6.22 (s, 1H), 3.41-3.32 (m, 2H), 3.08 (t, J=11.4 Hz, 2H), 2.19-2.11 (m, 2H), 1.75 (d, J=13.5 Hz, 2H).

Example 3: 8-(7-Chloroimidazo[1,5-a]pyridin-5-yl)-1,3,8-triazaspiro[4.5]decane-2,4-dione

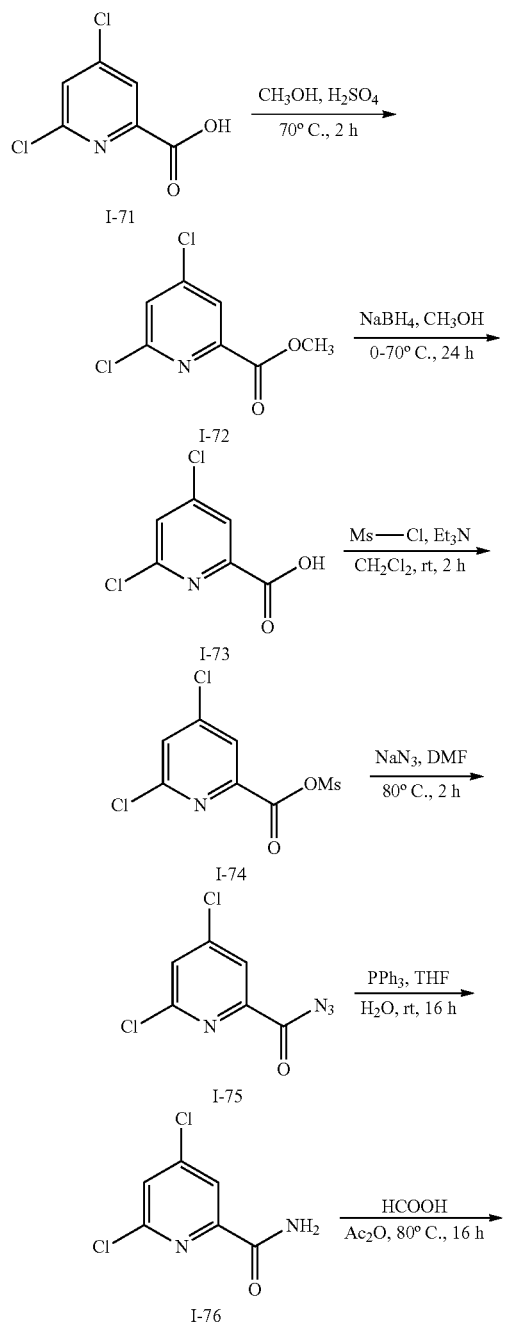

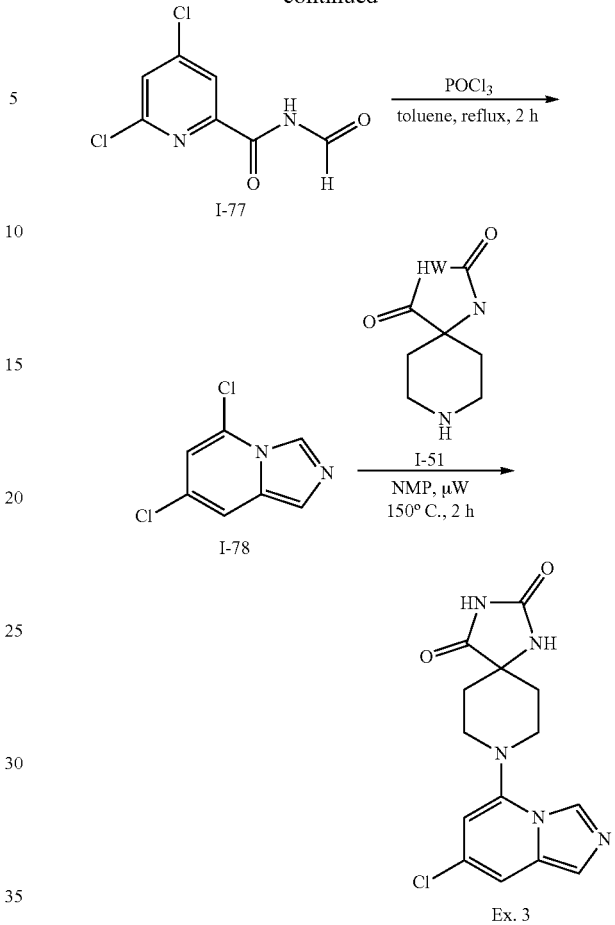

Preparation of I-72:

A stirred solution of I-71 (20.0 g, 104.1 mmol) in CH₃OH (200 mL) was charged with conc H₂SO₄ (1.0 mL) at RT. The reaction mixture was heated at 70° C. for 2 h. The reaction mixture was concentrated under reduced pressure, diluted with EtOAc (100 mL) and poured into saturated NaHCO₃ solution (80 mL). The layers were separated and the aqueous layer was extracted with EtOAc (2×150 mL). The combined organic layer was washed with water (100 mL) and brine (100 mL). The organic layer was dried over anhydrous Na₂SO₄ and concentrated under reduced pressure to afford I-72 as a liquid.

MS (MM) m/z 207.1 [M+H]⁺.

Preparation of I-73:

A stirred solution of I-72 (20.0 g, 97 mmol) in CH₃OH (80 mL) was charged with NaBH₄ (14.35 g, 388 mmol) portion wise for 15 min at 0° C. The reaction mixture was stirred at 70° C. for 24 h. The reaction mixture was cooled to RT, concentrated under reduced pressure and partitioned between water (200 mL) and EtOAc (3×300 mL). The combined organic layer was washed with water (100 mL) and brine (100 mL). The organic layer was dried over anhydrous Na₂SO₄ and concentrated in vacuo to afford I-73 as a solid. MS (MM) m/z 179.1 [M+H]⁺.

Preparation of I-74:

A solution of I-73 (18.5 g, 103.9 mmol) in CH₂Cl₂ (80 mL) at 0° C. was charged with Et₃N (28 mL, 207.8 mmol) followed by MsCl (12 mL, 155.8 mmol). The reaction mixture was stirred at RT for 2 h. The reaction mixture was diluted with water (100 mL) and extracted with EtOAc (3×200 mL). The organic phase was separated, dried over anhydrous $Na_2SO_4$ and concentrated in vacuo to afford I-74 [20.0 g (crude)] as a solid, which was used for the next step without further purification.

MS (MM) m/z 256.1 $[M+H]^+$.

Preparation of I-75:

A solution of I-74 (20.0 g, 78 mmol) in DMF (80 mL) was charged with $NaN_3$ (15.2 g, 235 mmol) at RT. The reaction mixture was heated at 80° C. for 2 h. The reaction mixture was diluted with cold water (100 mL) and extracted with MTBE (3×200 mL). The organic phase was separated, dried over anhydrous $Na_2SO_4$ and concentrated in vacuo to afford I-75 as a liquid.

Preparation of I-76:

A stirred solution of I-75 (11.0 g, 54.4 mmol) in THF (90 mL) and water (9.0 mL) was charged with $PPh_3$ (17.0 g, 65.3 mmol) at RT portion wise for 5 min. The reaction mixture was stirred at RT for 16 h. The reaction mixture was concentrated under reduced pressure. The residue was diluted with water (80 mL) and extracted with $CH_2Cl_2$ (2×50 mL). Aqueous layer was separated, acidified with HCl (2 N, 20 mL) and concentrated in vacuo to afford HCl salt of I-76 as a solid. MS (MM) m/z 177.1 $[M+H]^+$.

Preparation of I-77:

A stirred solution of I-76 (6.00 g, 34 mmol) in $HCO_2H$ (100 mL) was charged with $Ac_2O$ (20 mL) at RT. The reaction mixture was stirred at 80° C. for 16 h. The reaction mixture was concentrated under reduced pressure and co-evaporated with toluene (2×30 mL) to afford I-77 as a solid. MS (MM) m/z 205.1 [M+H]+.

Preparation of I-78:

A stirred solution of I-77 (1.20 g, 5.8 mmol) in toluene (10 mL) was charged with $POCl_3$ (1.2 mL) at 0° C. The reaction mixture was heated at 100° C. for 2 h. The reaction mixture was concentrated under reduced pressure, diluted with water (50 mL), basified with aqueous NaOH solution (6 N, 20 mL) and was extracted with EtOAc (3×100 mL). The organic phase was separated, dried over anhydrous $Na_2SO_4$ and concentrated in vacuo. The residue was purified by combi-flash column chromatography using Redisep® column (12 g, hexanes/EtOAc, 8:2) to afford I-78 as a solid.

Preparation of Ex. 3:

A solution of I-78 (60.0 mg, 0.32 mmol) and I-51 (548 mg, 3.2 mmol) in NMP (1.0 mL) was irradiated under microwave at 150° C. for 2 h. The reaction mixture was diluted with cold water (3.0 mL) and extracted with EtOAc (3×8.0 mL). The organic layer was separated, dried over anhydrous $Na_2SO_4$ and concentrated in vacuo. The residue was purified by combiflash column chromatography using Redisep® column (4 g, EtOAc/hexanes, 9:1) to afford Ex. 3 as a solid. MS (MM) m/z 320.1 $[M+H]^+$.

$^1$H NMR (400 MHz, DMSO-$d_6$): δ 10.77 (s, 1H), 8.59 (s, 1H), 8.28 (s, 1H), 7.48 (s, 1H), 7.39 (s, 1H), 6.14 (s, 1H), 3.08 (t, J=12.0 Hz, 4H), 2.15 (t, J=11.6 Hz, 2H), 1.76 (d, J=13.2 Hz, 2H).

Example 4: 8-(6-(Trifluoromethyl)imidazo[1,5-a]pyridin-8-yl)-1,3,8-triazaspiro[4.5]decane-2,4-dione

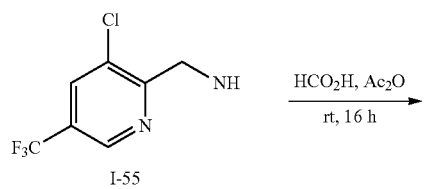

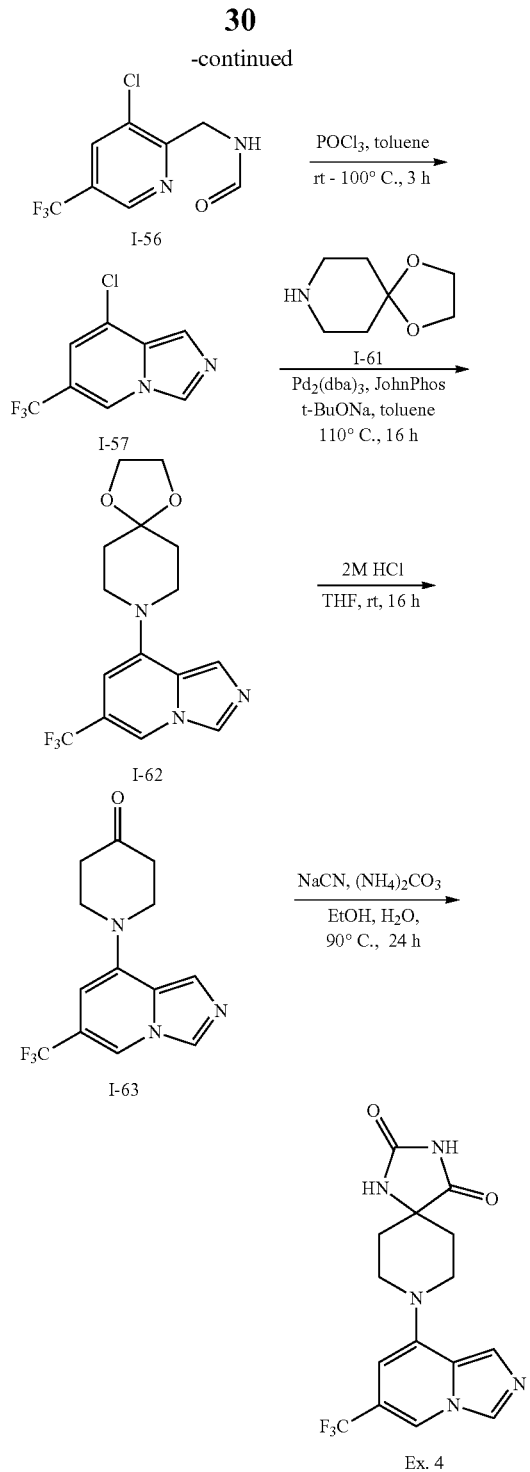

Preparation of I-56:

A stirred solution of I-55 (5.00 g, 23.91 mmol) in $HCO_2H$ (50 mL) was charged with $Ac_2O$ (50 mL) at RT. The reaction mixture was stirred at RT for 16 h. The reaction mixture was concentrated under reduced pressure and co-evaporated with toluene (2×100 mL) to afford I-56 as a solid. MS (MM) m/z 239.1 $[M+H]^+$.

Preparation of I-57:

A stirred solution of I-56 (5.00 g, 20.99 mmol) in toluene (25 mL) was charged with POCl$_3$ (2.5 mL) at RT. The reaction mixture was heated at 100° C. for 3 h. The reaction mixture was cooled, diluted with EtOAc (500 mL) and poured into aqueous NaOH solution (6 N, 10 mL). The layers were separated and the aqueous layer was extracted with EtOAc (3×50 mL). The combined organic layers were washed with water (200 mL) and brine (200 mL). The organic layer was dried over anhydrous Na$_2$SO$_4$ and concentrated in vacuo to afford I-57 as a solid. MS (MM) m/z 221.1 [M+H]$^+$.

Preparation of I-62:

A stirred solution of I-57 (1.00 g, 4.5 mmol) in toluene (10 mL) was charged with I-61 (700 mg, 4.9 mmol) and t-BuONa (864 mg, 9.0 mmol) at RT. The reaction mixture was purged with argon for 20 min. Pd$_2$(dba)$_3$ (823 mg, 0.89 mmol) and JohnPhos (40.0 mg, 0.13 mmol) were added to the reaction mixture and refluxed to 110° C. for 16 h. The reaction mixture was cooled to RT and concentrated under reduced pressure. The resultant slurry was diluted with EtOAc (100 mL) and washed with brine (2×75 mL). The organic phase was separated, dried over anhydrous Na$_2$SO$_4$, filtered and concentrated in vacuo to afford a residue. The residue was purified by combiflash column chromatography using Redisep® column (12 g, EtOAc/hexanes, 4:1) to afford I-62 as a solid. MS (MM) m/z 328.1 [M+H]$^+$.

Preparation of I-63:

A stirred solution of I-62 (180 g, 5.5 mmol) in THF (10 mL) was charged with HCl (2 M, 5.0 mL) at RT. The reaction mixture was stirred for 16 h at the same temperature. The reaction mixture was diluted with water (10 mL) and extracted with EtOAc (2×30 mL). The aqueous layer was separated, basified with aqueous NaOH (6 N, 10 mL) and extracted with EtOAc (2×30 mL). The organic phase was separated, dried over anhydrous Na$_2$SO$_4$, filtered and concentrated in vacuo to afford I-63 as a solid. MS (MM) m/z 284.1 [M+H]$^+$ Preparation of Ex. 4:

A stirred solution of I-63 (110 mg, 0.38 mmol) in a mixture of EtOH (5.0 mL) and H$_2$O (3.0 mL) was charged with NaCN (75.0 mg, 1.57 mmol) and (NH$_4$)$_2$CO$_3$ (754 mg, 7.67 mmol) at RT. The reaction mixture was heated at 90° C. for 24 h in a sealed tube. The reaction mixture was cooled to RT, diluted with water (20 mL) and extracted with EtOAc (3×30 mL). The organic phase was separated, washed with brine (5×20 mL), dried over anhydrous Na$_2$SO$_4$ and was concentrated under reduced pressure. The crude compound was stirred with MTBE (20 mL) and filtered to afford Ex. 4 as a solid. MS (MM) m/z 354.1 [M+H]$^+$.

$^1$H NMR (400 MHz, DMSO-d$_6$): δ 10.74 (s, 1H), 8.63 (s, 1H), 8.56 (s, 1H), 8.48 (s, 1H), 7.56 (s, 1H), 6.13 (s, 1H), 3.66 (d, J=12.4 Hz, 2H), 3.16 (t, J=8.1 Hz, 2H), 2.09-2.03 (m, 2H), 1.72 (d, J=10.2 Hz, 2H).

Example 5: 6,6-Dimethyl-8-(7-(trifluoromethyl) imidazo[1,5-a]pyridin-5-yl)-1,3,8-triazaspiro[4.5] decane-2,4-dione

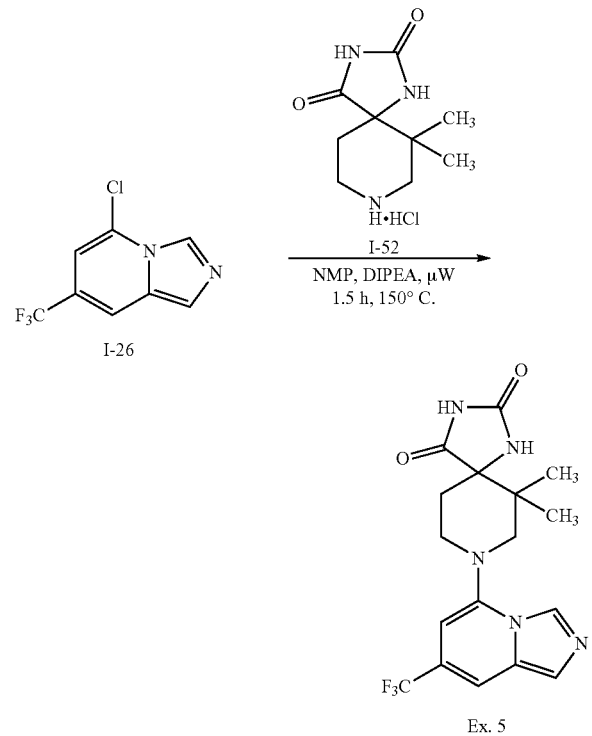

Preparation of Ex. 5:

A solution of I-26 (150 mg, 0.90 mmol), I-52 (166 mg, 0.99 mmol) and DIPEA (340 mg, 2.7 mmol) in NMP (1.0 mL) was irradiated under microwave at 150° C. for 1.5 h. The reaction mixture was diluted with EtOAc (30 mL). The organic layer was washed with brine (3×50 mL). The organic layer was separated, dried over anhydrous Na$_2$SO$_4$ and concentrated under reduced pressure to afford crude. The residue was further purified by combiflash column chromatography using Redisep® column (4 g, CH$_2$Cl$_2$/MeOH, 9:1) to afford Ex. 5 as a solid. MS (MM) m/z 382.1 [M+H]$^+$.

$^1$H NMR (400 MHz, DMSO-d$_6$): δ 10.74 (s, 1H), 8.46 (s, 1H), 8.27 (s, 1H), 7.89 (s, 1H), 7.73 (s, 1H), 6.28 (s, 1H), 3.28-3.24 (m, 3H), 3.03 (d, J=11.6 Hz, 2H), 2.17-2.06 (m, 2H), 1.07 (s, 6H).

Example 6: 3-Methyl-8-(7-(trifluoromethyl)imidazo [1,5-a]pyridin-5-yl)-1,3,8-triazaspiro[4.5]decane-2, 4-dione

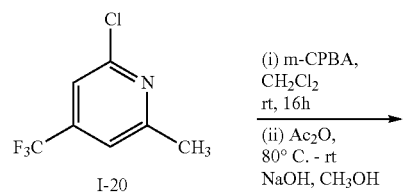

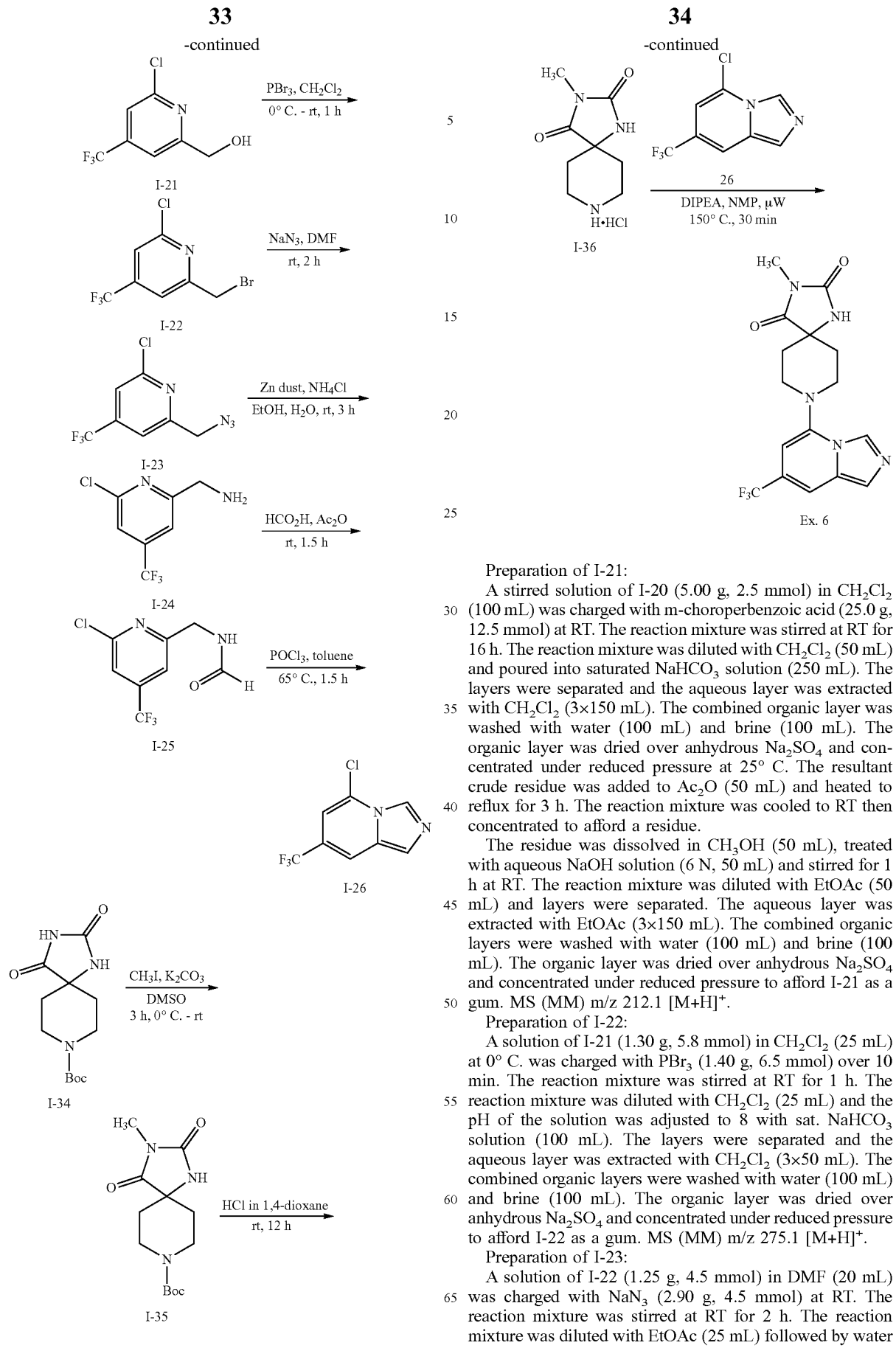

Preparation of I-21:

A stirred solution of I-20 (5.00 g, 2.5 mmol) in CH$_2$Cl$_2$ (100 mL) was charged with m-choroperbenzoic acid (25.0 g, 12.5 mmol) at RT. The reaction mixture was stirred at RT for 16 h. The reaction mixture was diluted with CH$_2$Cl$_2$ (50 mL) and poured into saturated NaHCO$_3$ solution (250 mL). The layers were separated and the aqueous layer was extracted with CH$_2$Cl$_2$ (3×150 mL). The combined organic layer was washed with water (100 mL) and brine (100 mL). The organic layer was dried over anhydrous Na$_2$SO$_4$ and concentrated under reduced pressure at 25° C. The resultant crude residue was added to Ac$_2$O (50 mL) and heated to reflux for 3 h. The reaction mixture was cooled to RT then concentrated to afford a residue.

The residue was dissolved in CH$_3$OH (50 mL), treated with aqueous NaOH solution (6 N, 50 mL) and stirred for 1 h at RT. The reaction mixture was diluted with EtOAc (50 mL) and layers were separated. The aqueous layer was extracted with EtOAc (3×150 mL). The combined organic layers were washed with water (100 mL) and brine (100 mL). The organic layer was dried over anhydrous Na$_2$SO$_4$ and concentrated under reduced pressure to afford I-21 as a gum. MS (MM) m/z 212.1 [M+H]$^+$.

Preparation of I-22:

A solution of I-21 (1.30 g, 5.8 mmol) in CH$_2$Cl$_2$ (25 mL) at 0° C. was charged with PBr$_3$ (1.40 g, 6.5 mmol) over 10 min. The reaction mixture was stirred at RT for 1 h. The reaction mixture was diluted with CH$_2$Cl$_2$ (25 mL) and the pH of the solution was adjusted to 8 with sat. NaHCO$_3$ solution (100 mL). The layers were separated and the aqueous layer was extracted with CH$_2$Cl$_2$ (3×50 mL). The combined organic layers were washed with water (100 mL) and brine (100 mL). The organic layer was dried over anhydrous Na$_2$SO$_4$ and concentrated under reduced pressure to afford I-22 as a gum. MS (MM) m/z 275.1 [M+H]$^+$.

Preparation of I-23:

A solution of I-22 (1.25 g, 4.5 mmol) in DMF (20 mL) was charged with NaN$_3$ (2.90 g, 4.5 mmol) at RT. The reaction mixture was stirred at RT for 2 h. The reaction mixture was diluted with EtOAc (25 mL) followed by water (100 mL). The layers were separated and the aqueous layer was extracted with EtOAc (3×50 mL). The combined organic layers were washed with water (100 mL) and brine (100 mL). The organic layer was dried over anhydrous $Na_2SO_4$ and concentrated under reduced pressure to afford I-23 as a gum. MS (MM) m/z 237.1 $[M+H]^+$.

Preparation of I-24:

A solution of I-23 (1.05 g, 4.6 mmol) in EtOH (20 mL) and $H_2O$ (20 mL) was charged with Zn powder (3.00 g, 4.6 mmol) followed by $NH_4Cl$ (2.47 g, 4.6 mmol) at RT. The reaction mixture was stirred at RT for 3 h. The reaction mixture was filtered through Celite® bed and washed with $CH_2Cl_2$ (100 mL). The layers were separated and the aqueous layer was extracted with $CH_2Cl_2$ (3×50 mL). The combined organic layers were washed with water (100 mL) and brine (100 mL). The organic layers were dried over anhydrous $Na_2SO_4$ and concentrated under reduced pressure to afford I-24 as a solid. MS (MM) m/z 211.1 $[M+H]^+$.

Preparation of I-25:

A stirred solution of I-24 (900 mg, 4.2 mmol) in $HCO_2H$ (25 mL) was charged with $Ac_2O$ (5.0 mL) at RT. The reaction mixture was stirred at RT for 1.5 h. The reaction mixture was concentrated under reduced pressure and then co-evaporated with toluene (2×50 mL) to afford I-25 as a solid. MS (MM) m/z 239.1 $[M+H]^+$.

Preparation of I-26:

A stirred solution of I-25 (1.00 g, 4.2 mmol) in toluene (10 mL) was charged with $POCl_3$ (0.5 mL) at RT. The reaction mixture was heated at 65° C. for 1.5 h. The reaction mixture was cooled, diluted with EtOAc (50 mL) and poured into aqueous NaOH solution (1 N, 50 mL). The layers were separated and the aqueous layer was extracted with EtOAc (3×50 mL). The combined organic layers were washed with water (100 mL) and brine (100 mL). The organic layer was dried over anhydrous $Na_2SO_4$ and concentrated in vacuo to afford I-26 as a solid. MS (MM) m/z 221.1 $[M+H]^+$.

Preparation of I-35:

A stirred solution of I-34 (500 mg, 1.85 mmol) in DMSO (10 mL) at 0° C. was charged with methyl iodide (0.29 mg, 2.04 mmol) and $K_2CO_3$ (765 mg, 5.55 mmol). The reaction mixture was warmed to RT and stirred for 3 h. Water (20 mL) was added to the reaction mixture and extracted with EtOAc (3×20 mL). The organic phase was collected, washed with brine (3×20 mL), dried over anhydrous $Na_2SO_4$ and concentrated under reduced pressure. The resultant crude product was stirred with MTBE (10 mL) and filtered to afford I-35 as a solid. MS (MM) m/z 284.1 $[M+H]^+$.

Preparation of I-36:

A mixture of I-35 (170 mg, 6.2 mmol) and HCl in 1,4-dioxane (4 M, 5.0 mL) was stirred at RT for 12 h. The solvent was evaporated under reduced pressure to afford I-36 as a solid.

Preparation of Ex. 6:

A solution of I-36 (100 mg, 0.45 mmol), I-26 (82.0 mg, 0.45 mmol) and DIPEA (250 mg, 0.9 mmol) in NMP (1.0 mL) was irradiated under microwave at 150° C. for 30 min. The reaction mixture was cooled to RT, diluted with EtOAc (30 mL) and washed with brine (3×50 mL). The organic layer was collected, dried over anhydrous $Na_2SO_4$, concentrated and dried under reduced pressure. The resultant crude compound was purified by combiflash column chromatography using Redisep® column (4 g, 100% EtOAc) to afford Ex. 6 as a solid. MS (MM) m/z 368.1 $[M+H]^+$ $^1H$ NMR (400 MHz, DMSO-$d_6$): δ 8.86 (s, 1H), 8.75 (s, 1H), 7.96 (s, 1H), 7.86 (s, 1H), 6.36 (s, 1H), 3.44 (d, J=12.4 Hz, 2H), 3.15 (t, J=11.6 Hz, 2H), 2.22 (t, J=10.8 Hz, 1H), 1.77 (d, J=13.2 Hz, 2H).

Example 7: 3-((Tetrahydro-2H-pyran-4-yl)methyl)-8-(7-(trifluoromethyl)imidazo[1,5-a]pyridin-5-yl)-1,3,8-triazaspiro[4.5]decane-2,4-dione

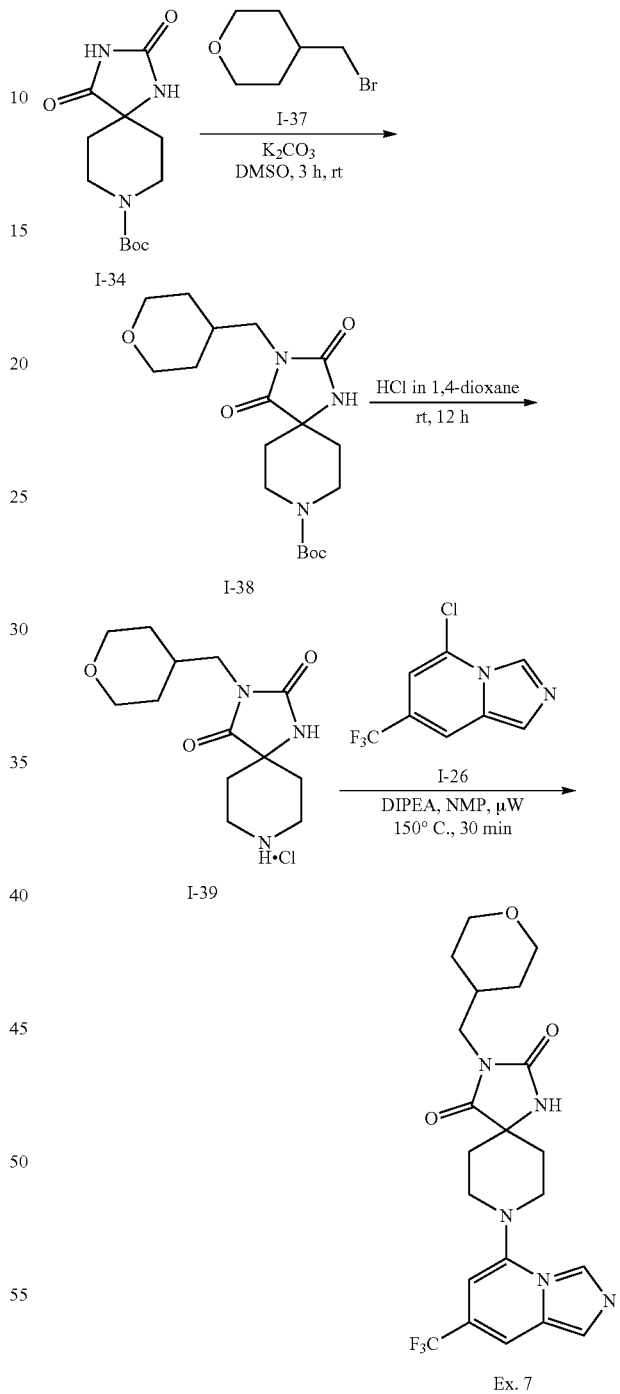

Preparation of I-38:

A stirred solution of I-34 (500 mg, 1.85 mmol) in DMSO (10 mL) was charged with I-37 (0.29 mg, 2.04 mmol) and $K_2CO_3$ (765 mg, 5.55 mmol) at 0° C. The reaction mixture was stirred for 3 h at RT. The reaction mixture was treated with water (20 mL) and extracted with EtOAc (3×20 mL). The organic phase was collected, washed with brine (3×20 mL), dried over anhydrous Na₂SO₄ and evaporated under reduced pressure. The resultant crude residue was stirred with MTBE (10 mL) and filtered to afford I-38 as a solid. MS (MM) m/z 368.1 [M+H]⁺.

Preparation of I-39:

A mixture of I-38 (170 mg, 6.2 mmol) and HCl in 1,4-dioxane (4 M, 5.0 mL) was stirred at RT for 12 h. The solvent was evaporated under reduced pressure to afford I-39 as a solid.

Preparation of Ex. 7:

A solution of I-26 (100 mg, 0.45 mmol), I-39 (130 mg, 0.45 mmol) and DIPEA (250 mg, 0.9 mmol) in NMP (1.0 mL) was irradiated under microwave at 150° C. for 30 min. The reaction mixture was cooled to RT, diluted with EtOAc (30 mL) and washed with brine (3×50 mL). The organic layer was collected, dried over anhydrous Na₂SO₄ and concentrated under reduced pressure. The resultant crude compound was stirred with MTBE (20 mL) and filtered to afford Ex. 7 as a solid. MS (MM) m/z 452.1 [M+H]⁺.

¹H NMR (300 MHz, DMSO-d₆): δ 8.91 (s, 1H), 8.50 (s, 1H), 7.90 (s, 1H), 7.73 (s, 1H), 6.27 (s, 1H), 3.83 (d, J=9.0 Hz, 2H), 3.45 (t, J=12.3 Hz, 2H), 3.30-3.11 (m, 6H), 2.23 (t, J=14.7 Hz, 2H), 1.92-1.80 (m, 1H), 1.78 (d, J=13.2 Hz, 2H), 1.49 (d, J=11.1 Hz, 2H), 1.24-1.16 (m, 2H).

Example 8: 8-(7-Chloroimidazo[1,5-a]pyridin-5-yl)-6,6-dimethyl-1,3,8-triazaspiro[4.5]decane-2,4-dione chromatography using Redisep® column (4 g, EtOAc/hexanes, 7:3) to afford Ex. 8 as a solid. MS (MM) m/z 346.1 [M−H]⁻.

¹H NMR (300 MHz, DMSO-d₆): δ 8.17 (s, 1H), 7.30 (s, 1H), 7.28 (s, 1H), 6.17 (s, 1H), 3.38-3.30 (m, 3H), 2.87 (d, J=12.3 Hz, 1H), 2.16-2.05 (m, 2H), 1.14 (s, 3H), 1.02 (s, 3H).

Example 9: 3-Phenyl-8-(7-(trifluoromethyl)imidazo[1,5-a]pyridin-5-yl)-1,3,8-triazaspiro[4.5]decane-2,4-dione

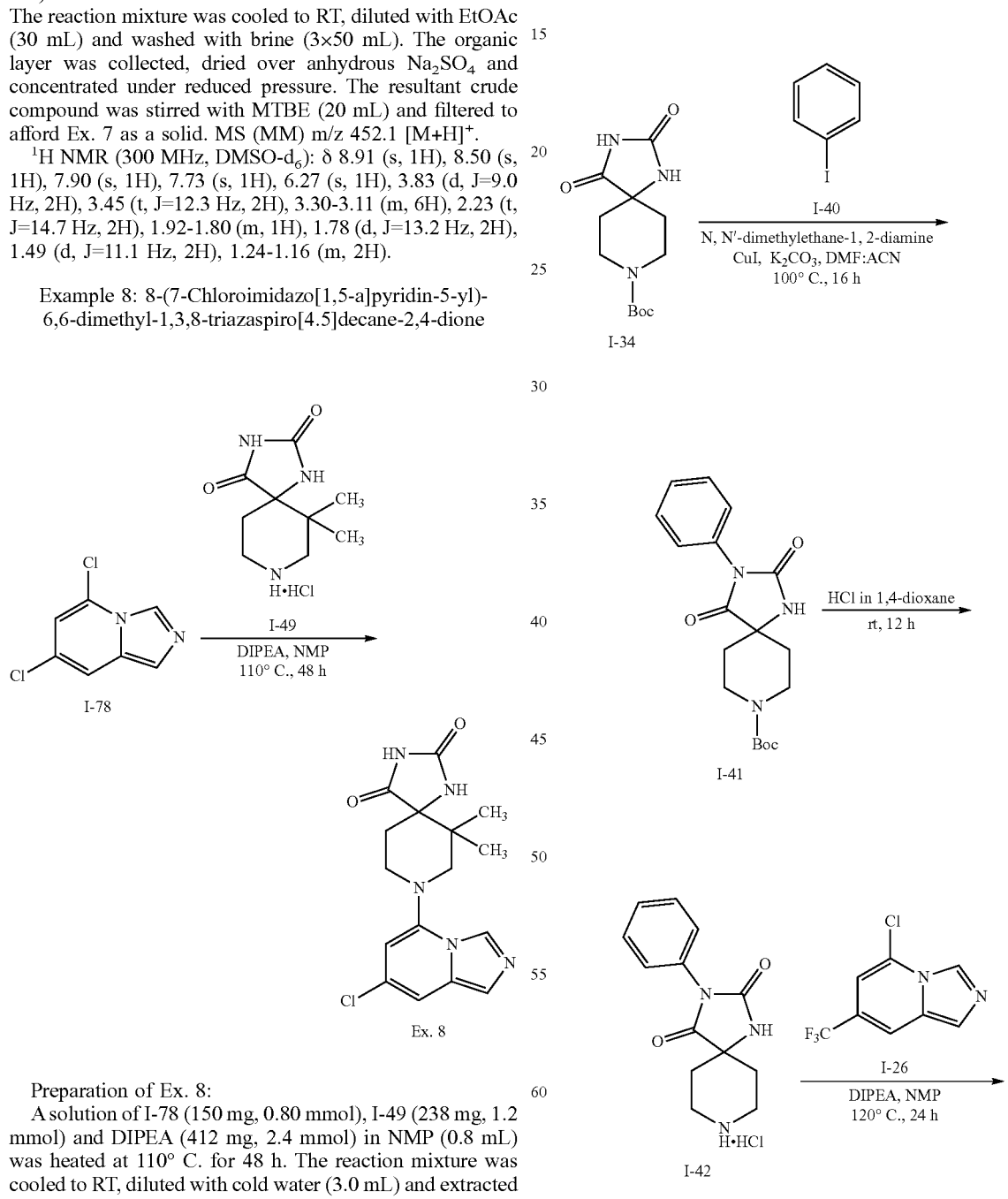

Preparation of Ex. 8:

A solution of I-78 (150 mg, 0.80 mmol), I-49 (238 mg, 1.2 mmol) and DIPEA (412 mg, 2.4 mmol) in NMP (0.8 mL) was heated at 110° C. for 48 h. The reaction mixture was cooled to RT, diluted with cold water (3.0 mL) and extracted with EtOAc (3×10 mL). The organic phase was separated, dried over anhydrous Na₂SO₄ and concentrated in vacuo. The residue was further purified by combiflash column

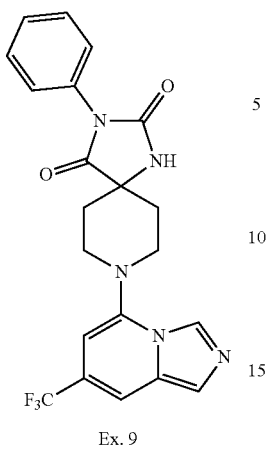

Ex. 9

Preparation of I-41:

A stirred solution of I-34 (500 mg, 1.85 mmol) in a mixture of acetonitrile (20 mL) and DMF (20 mL) was charged with I-40 (483 mg, 0.33 mmol) K$_2$CO$_3$ (765 mg, 2.2 mmol), N,N'-dimethylethane-1,2-diamine (93.0 mg, 0.55 mmol) and CuI (200 mg, 0.55 mmol) at RT. The reaction mixture was stirred at 100° C. for 16 h. The reaction mixture was diluted with water (50 mL) and extracted with EtOAc (5×20 mL). The organic phase was collected and washed with brine (5×20 mL). The organic phase was dried over anhydrous Na$_2$SO$_4$ and evaporated under reduced pressure. The resultant residue was purified by combiflash column chromatography using Redisep® column (12 g, 100% EtOAc) to afford I-41 as a solid. MS (MM) m/z 368.1 [M+H]$^+$.

Preparation of I-42:

A mixture of I-41 (170 mg, 6.2 mmol) and HCl in 1,4-dioxane (4 M, 5.0 mL) was stirred at RT for 12 h. The solvent was evaporated under reduced pressure to afford I-42 as a solid. MS (MM) m/z 346.1 [M+H]$^+$.

Preparation of Ex. 9:

A solution of I-26 (100 mg, 0.45 mmol), I-42 (130 mg, 0.45 mmol) and DIPEA (250 mg, 0.9 mmol) in NMP (1.0 mL) was heated at 120° C. for 24 h. The reaction mixture was cooled to RT, diluted with EtOAc (30 mL) and washed with brine (3×50 mL). The reaction mixture was dried over anhydrous Na$_2$SO$_4$, concentrated and dried under reduced pressure. The resultant residue was purified by combiflash column chromatography using Redisep® column (4 g, CH$_2$Cl$_2$/MeOH, 9:1) to afford Ex. 9 as a solid. MS (MM) m/z 430.1 [M+H]$^+$.

$^1$H NMR (400 MHz, DMSO-d$_6$): δ 9.15 (s, 1H), 8.53 (s, 1H), 7.91 (s, 1H), 7.74 (s, 1H), 7.52-7.48 (m, 2H), 7.43-7.39 (m, 3H), 6.30 (s, 1H), 3.51-3.50 (m, 2H), 3.21 (d, J=11.6 Hz, 2H), 2.35-2.28 (m, 2H), 1.99 (m, 2H).

Example 10: 3,6,6-Trimethyl-8-(7-(trifluoromethyl) imidazo[1,5-a]pyridin-5-yl)-1,3,8-triazaspiro[4.5] decane-2,4-dione

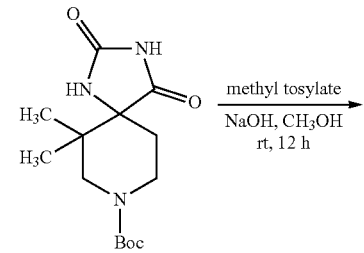

I-43

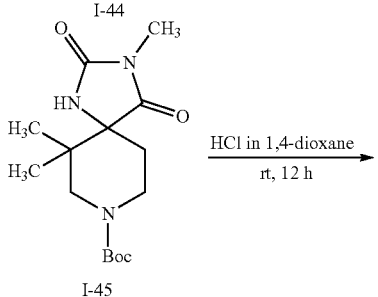

I-44

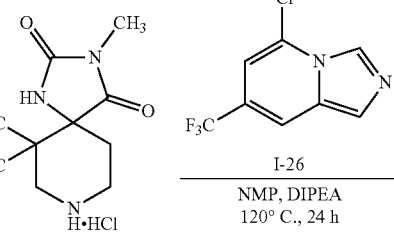

I-45

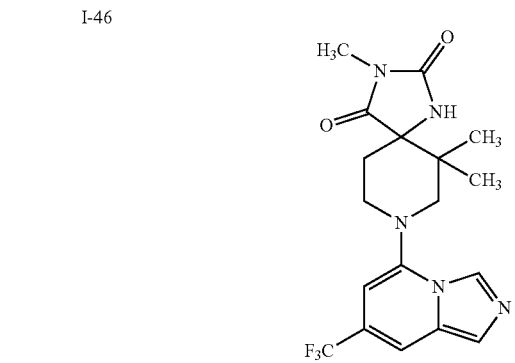

Ex. 10

Preparation of I-44:

A stirred solution of I-43 (7.00 g, 30.8 mmol) in EtOH (140 mL) and H$_2$O (40 mL) was charged with NaCN (3.00 g, 61.6 mmol) and ammonium carbonate (59.1 g, 616 mmol) at RT. The reaction mixture was stirred at 80° C. for 12 h in a sealed tube. The reaction mixture was diluted with water (200 mL) and extracted with EtOAc (3×150 mL). The organic phase was washed with brine (5×20 mL), dried over anhydrous Na$_2$SO$_4$ and evaporated under reduced pressure to afford I-44 as a solid. MS (MM) m/z 368.1 [M+H]$^+$.

Preparation of I-45:

A stirred solution of I-44 (1.00 g, 3.3 mmol) in CH$_3$OH (140 mL) was charged with methyl tosylate (1.37 g, 7.4 mmol) and NaOH (230 mg, 5.94 mmol) at RT. The reaction mixture was stirred for 12 h at RT. The reaction mixture was treated with water (30 mL) and extracted with CH$_2$Cl$_2$ (3×30 mL). The combined organic layer was dried over anhydrous Na$_2$SO$_4$ and evaporated to afford I-45 as a solid which was used for next step without further purification.

Preparation of I-46:

A mixture of I-45 (350 mg, 6.2 mmol) and HCl in 1,4-dioxane (4 M, 10 mL) was stirred at RT for 12 h. The solvent was evaporated under reduced pressure to afford I-46 as a solid.

Preparation of Ex. 10:

A solution of I-26 (200 mg, 0.45 mmol), I-46 (178 mg, 0.49 mmol) and DIPEA (348 mg, 1.35 mmol) in NMP (1.0 mL) was heated at 120° C. for 24 h. The reaction mixture was cooled to RT, diluted with EtOAc (30 mL) and washed with brine (3×50 mL). The organic layer was collected, dried over anhydrous Na$_2$SO$_4$, concentrated and dried under reduced pressure. The resultant residue was purified by combiflash column chromatography using Redisep® column (12 g, CH$_2$Cl$_2$/MeOH, 9:1) to afford Ex. 10 as a solid. MS (MM) m/z 396.1 [M+H]$^+$.

$^1$H NMR (300 MHz, DMSO-d$_6$): δ 8.57 (s, 1H), 8.48 (s, 1H), 7.89 (s, 1H), 7.73 (s, 1H), 6.29 (s, 1H), 3.40-3.25 (m, 3H), 3.05 (d, J=11.7 Hz, 1H), 2.85 (s, 3H), 2.11-2.07 (m, 2H), 1.05 (s, 6H).

Example 11: 8-(7-Chloroimidazo[1,5-a]pyridin-5-yl)-6,6-dimethyl-1,3,8-triazaspiro[4.5]decane-2,4-dione

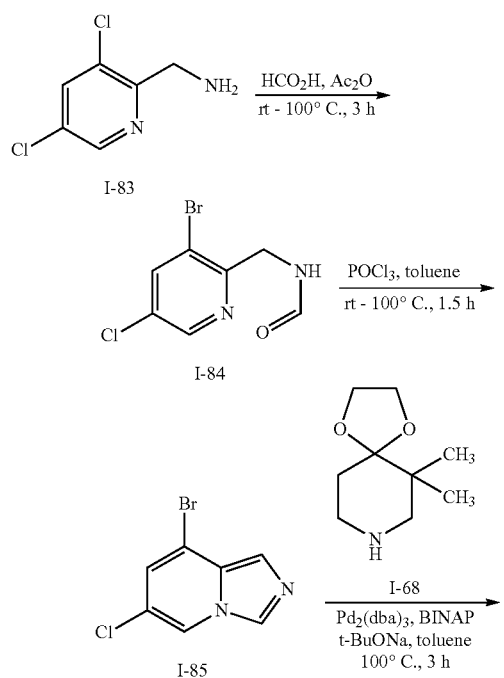

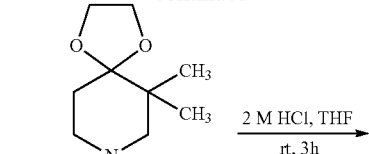

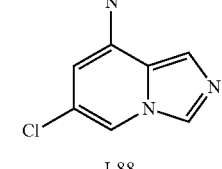

I-88

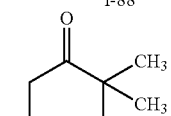

I-89

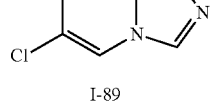

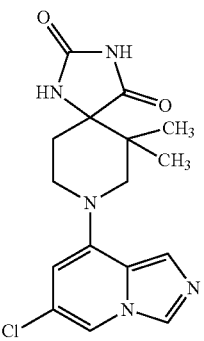

Ex. 11

Preparation of I-84:

A stirred solution of I-83 (15.0 g, 71.0 mmol) in HCO$_2$H (370 mL) was charged with Ac$_2$O (750 mL) at RT. The reaction mixture was stirred at 100° C. for 1.5 h. The reaction mixture was concentrated under reduced pressure and co-evaporated with toluene (2×100 mL) to afford I-84 as a solid. MS (MM) m/z 249.1 [M+H]$^+$.

Preparation of I-85:

A stirred solution of I-84 (13.0 g, 54.0 mmol) in toluene (100 mL) was charged with POCl$_3$ (6.0 mL) at RT. The reaction mixture was heated at 100° C. for 1.5 h. The reaction mixture was cooled, diluted with EtOAc (300 mL) and poured into aqueous NaOH solution (1 N, 300 mL). The layers were separated and the aqueous layer was extracted with EtOAc (3×300 mL). The combined organic layers were washed with water (2×200 mL) and brine (200 mL). The organic layer was dried over anhydrous Na$_2$SO$_4$ and concentrated in vacuo to afford I-85 as a solid. MS (MM) m/z 230.4 [M+H]$^+$.

Preparation of I-88:

A stirred solution of I-85 (800 mg, 3.45 mmol) in toluene (20 mL) was charged with I-68 (590 mg, 3.45 mmol) and powdered t-BuONa (662 mg, 6.9 mmol) at RT. The reaction mixture was purged with argon for 20 min. Pd$_2$(dba)$_3$ (315 mg, 0.345 mmol) and BINAP (214 mg, 0.345 mmol) were added to the mixture and refluxed to 100° C. for 3 h. The reaction mixture was cooled to RT and concentrated under reduced pressure. The resultant slurry was diluted with EtOAc (100 mL) and washed with brine (2×75 mL). The organic phase was separated, dried over anhydrous Na$_2$SO$_4$, filtered and concentrated in vacuo to afford a residue. The residue was purified by combiflash column chromatography using Redisep® column (24 g, hexanes/EtOAc, 1:1) to afford I-88 as a solid. MS (MM) m/z 322.0 [M+H]$^+$.

Preparation of I-89:

A stirred solution of I-88 (600 mg, 1.86 mmol) in THF (3.0 mL) was charged with HCl (2 M, 3.0 mL) at RT. The reaction mixture was stirred for 3 h. The reaction mixture was basified with saturated NaHCO$_3$ solution (20 mL) and extracted with EtOAc (3×50 mL). The organic layer was dried over anhydrous Na$_2$SO$_4$ and concentrated in vacuo to afford I-89 as a solid.

Preparation of Ex. 11:

A solution of I-89 (380 mg, 1.3 mmol) in EtOH (8.0 mL) and water (4.0 mL) was placed in a sealed tube and charged with NaCN (134 mg, 2.73 mmol) and ammonium carbonate (2.10 g, 27.2 mmol) at RT. The reaction mixture was stirred at 100° C. for 16 h. The reaction mixture was poured into water (50 mL) and extracted with EtOAc (2×100 mL). The organic extracts were washed with water (2×50 mL) and brine (50 mL). The organic phase was separated, dried over anhydrous Na$_2$SO$_4$, filtered and concentrated in vacuo to afford Ex. 11 as a solid. MS (MM) m/z 348.1 [M+H]$^+$.

$^1$H NMR (300 MHz, DMSO-d$_6$): δ 10.70 (s, 1H), 8.30 (s, 1H), 8.22 (s, 1H), 8.20 (s, 1H), 7.44 (s, 1H), 6.06 (s, 1H), 3.45-3.42 (m, 1H), 3.39-3.30 (m, 2H), 3.17 (d, J=5.1 Hz, 1H), 2.01-1.95 (m, 2H).

Example 12: 6,6-Dimethyl-8-(6-(trifluoromethyl) imidazo[1,5-a]pyridin-8-yl)-1,3,8-triazaspiro[4.5] decane-2,4-dione

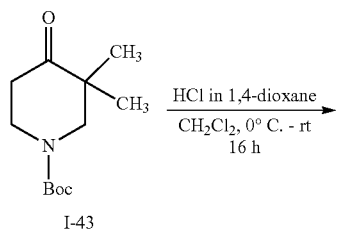

I-43

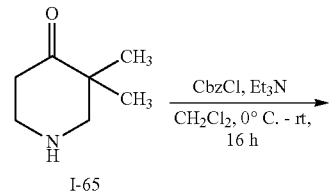

I-65

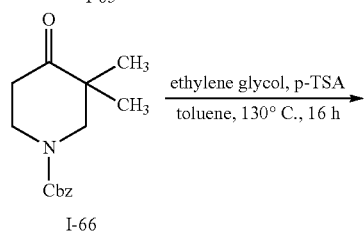

I-66

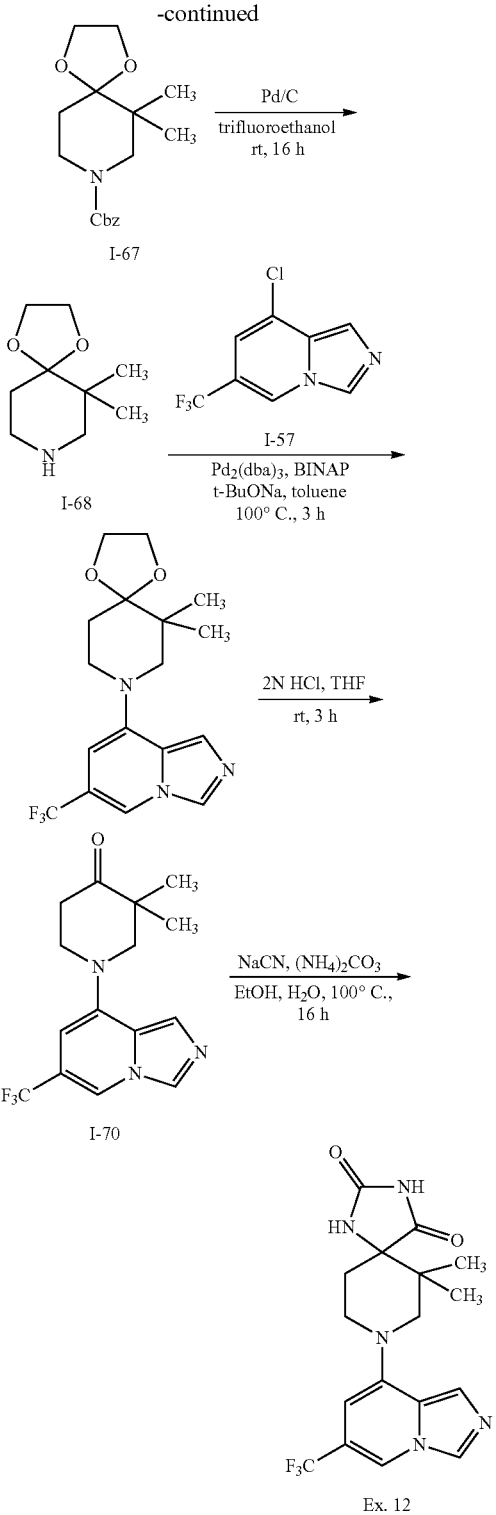

Preparation of I-65:

A solution of I-43 (5.00 g, 22.02 mmol) in CH$_2$Cl$_2$ (20 mL) was charged with HCl in 1,4-dioxane (4 M, 20 mL) over 15 min at 0° C. The reaction mixture was stirred at RT for 16 h. The solvent was concentrated under reduced pressure, co-distilled with MTBE (3×200 mL) to remove excess HCl and dried in vacuo to afford I-65 as an HCl salt. MS (MM) m/z 128.1 [M+H]$^+$.

Preparation of I-66:

A solution of I-65 (4.20 g, 33.07 mmol) in CH$_2$Cl$_2$ (80 mL) was charged with benzyl chloroformate (6.70 g, 39.68 mmol) followed by triethyl amine (5.00 g, 49 mmol) over 20 min at 0° C. The reaction mixture was stirred at RT for 16 h. The organic layer was washed with saturated NaHCO$_3$ solution (50 mL), water (100 mL) and brine (50 mL). The organic layer was concentrated under reduced pressure to afford I-66 as a liquid. MS (MM) m/z 262.1 [M+H]$^+$.

Preparation of I-67:

A stirred solution of I-66 (7.00 g, 26.7 mmol) in toluene (70 mL) was charged with ethylene glycol (1.98 g, 32 mmol) followed by p-TSA (28.0 mg, 1 mmol) at RT and the mixture was refluxed to 130° C. for 16 h. The reaction mixture was cooled to RT and concentrated under reduced pressure. The resultant slurry was diluted with EtOAc (100 mL) and washed with brine (2×500 mL). The organic phase was separated, dried over anhydrous Na$_2$SO$_4$, filtered and concentrated in vacuo to afford a residue. The residue was purified by combiflash column chromatography using Redisep® column (80 g, hexanes/EtOAc, 8:2) to afford I-67 as a liquid. MS (MM) m/z 172.0 [M+H]$^+$.

Preparation of I-68:

A stirred solution of I-67 (6.00 g, 305 mmol) in 2,2,2-trifluoroethanol (60 mL) was charged with Pd(OH)$_2$ (600 mg, 10 wt %) under argon atmosphere at RT. Hydrogen atmosphere was introduced using a balloon and the reaction mixture was stirred for 16 h. The reaction mixture was filtered through a Celite® bed, washed with CH$_3$OH (50 mL) and concentrated under reduced pressure to afford I-68 as an oil. MS (MM) m/z 172.0 [M+H]$^+$.

Preparation of I-69:

A stirred solution of I-57 (1.00 g, 4.54 mmol) in toluene (20 mL) was charged with I-68 (261 mg, 4.54 mmol) and powdered t-BuONa (872 mg, 9.0 mmol) at RT. The reaction mixture was purged with argon for 20 min. Pd$_2$(dba)$_3$ (415 mg, 0.45 mmol) and BINAP (282 mg, 0.45 mmol) were added to the reaction mixture and refluxed to 110° C. for 3 h. The reaction mixture was cooled to RT and concentrated under reduced pressure. The resultant slurry was diluted with EtOAc (100 mL) and washed with brine (2×75 mL). The organic phase was separated, dried over anhydrous Na$_2$SO$_4$, filtered and concentrated in vacuo to afford a residue. The residue was further purified by combiflash column chromatography using Redisep® column (24 g, hexanes/EtOAc, 1:1) to afford I-69 as a solid. MS (MM) m/z 356.1 [M+H]$^+$.

Preparation of I-70:

A stirred solution of I-69 (500 mg, 1.40 mmol) in THF (3.0 mL) was charged with HCl (2 N, 3.0 mL) at RT. The reaction mixture was stirred for 3 h. The reaction mixture was basified with saturated NaHCO$_3$ solution (20 mL) and extracted with EtOAc (3×50 mL). The organic layer was dried over anhydrous Na$_2$SO$_4$ and concentrated in vacuo to afford I-70 as a solid. MS (MM) m/z 312.1 [M+H]$^+$.

Preparation of Ex. 12:

A solution of I-70 (100 mg, 0.32 mmol) in a mixture of EtOH:H$_2$O (2:1, 12 mL) was charged with ammonium carbonate (500 mg, 6.42 mmol) followed by NaCN (31.0 mg, 0.642 mmol) at room temperature. The reaction mixture was stirred in a sealed tube at 100° C. for 16 h. The reaction mixture was cooled to room temperature and diluted with EtOAc (50 mL). The organic layer was washed with water (2×30 mL) and brine (20 mL). The organic phase was separated, dried over anhydrous Na$_2$SO$_4$, filtered and concentrated in vacuo to afford a dark brown residue. The residue was further purified by combiflash column chromatography using Redisep® column (12 g, DCM/MeOH, 9.7:0.3) to afford Ex. 12 as a solid. MS (MM) m/z 382.1 [M+H]$^+$.

$^1$H NMR (400 MHz, DMSO-d$_6$): δ 10.72 (s, 1H), 8.63 (s, 1H), 8.49 (s, 1H), 8.21 (s, 1H), 7.53 (s, 1H), 6.12 (s, 1H), 3.50-3.45 (m, 1H), 3.39-3.30 (m, 2H), 3.17 (d, J=12.4, 1H), 2.08-1.97 (m, 2H), 1.05 (d, J=1.2 Hz, 6H)

Example 13: 8-(7-(Trifluoromethyl)imidazo[1,5-a]pyridin-5-yl)-1,3,8-triazaspiro[4.5]decane-2,4-dione

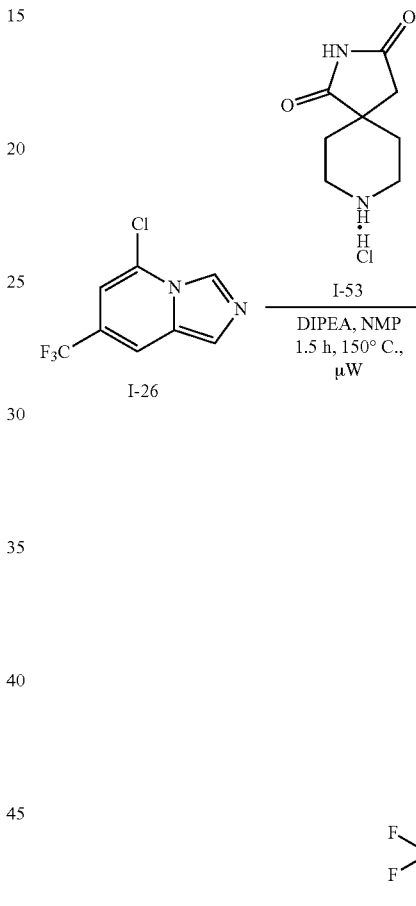

Ex. 13

Preparation of Ex. 13:

A solution of I-26 (100 mg, 0.45 mmol), I-53 (139 mg, 0.68 mmol) and DIPEA (175 mg, 1.36 mmol) in NMP (2.0 mL) was irradiated under microwave at 150° C. for 1.5 h. The reaction mixture was diluted with cold water (10 mL) and extracted with EtOAc (2×20 mL). The combined organic layer was washed with water (20 mL), brine (20 mL) and concentrated under reduced pressure. The residue was further purified by preparative TLC by using (CH$_2$Cl$_2$/CH$_3$OH, 98:2) to afford Ex. 13 as a solid. MS (MM) m/z 353[M+H]$^+$.

$^1$H NMR (400 MHz, DMSO-d$_6$): δ 8.44 (s, 1H), 7.88 (s, 1H), 7.72 (s, 1H), 6.30 (s, 1H), 3.42 (d, J=12.4 Hz, 2H), 2.91 (t, J=11.2 Hz, 2H), 2.69 (s, 2H), 2.16-2.08 (m, 2H), 1.79 (d, J=13.2 Hz, 2H).

Example 14: 6,6-Dimethyl-3-((tetrahydro-2H-pyran-4-yl)methyl)-8-(7-(trifluoromethyl)imidazo[1,5-a]pyridin-5-yl)-8-triazaspiro[4.5]decane-2,4-dione

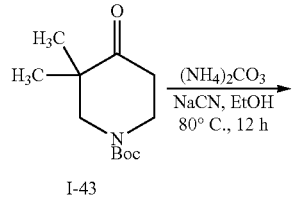

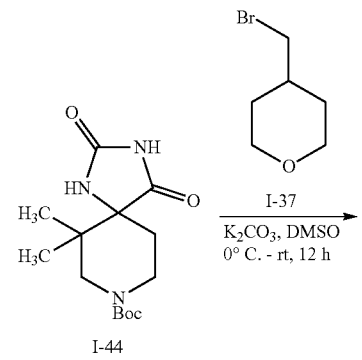

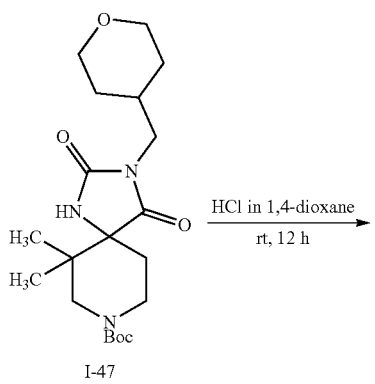

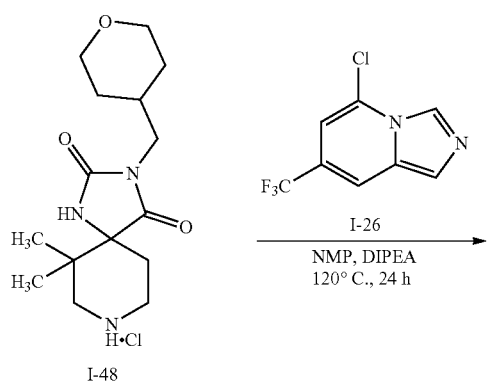

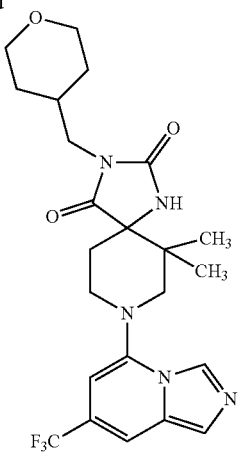

Ex. 14

Preparation of I-44:

A stirred solution of I-43 (7.00 g, 30.8 mmol) in EtOH (140 mL) and H₂O (40 mL) was charged with NaCN (3.00 g, 61.6 mmol) and ammonium carbonate (59.1, 616 mmol) at RT. The reaction mixture was stirred at 80° C. for 12 h in a sealed tube. The reaction mixture was cooled to RT, diluted with water (200 mL) and extracted with EtOAc (3×150 mL). The combined organic layer was washed with brine (5×20 mL), dried over anhydrous Na₂SO₄ and concentrated under reduced pressure to afford I-44 as a solid, which was used for next step without further purification. MS (MM) m/z 368.1 [M+H]⁺.

Preparation of I-47:

A stirred solution of I-44 (1.00 g, 3.35 mmol) in DMSO (10 mL) was charged with I-37 (660 mg, 2.04 mmol) and K₂CO₃ (1.38 g, 10.05 mmol) at 0° C. The reaction mixture was warmed to RT and stirred for 12 h. Water (20 mL) was added to the reaction mixture and extracted with EtOAc (3×20 mL). The combined organic phase was washed with brine (3×20 mL), dried over anhydrous Na₂SO₄ and evaporated under reduced pressure. The resultant residue was stirred with MTBE (10 mL) and filtered to afford I-47 as a solid.

Preparation of I-48:

A mixture of I-47 (1.20 g, 3.03 mmol) and HCl in 1,4-dioxane (4 M, 20 mL) was stirred at RT for 12 h. The solvent was evaporated under reduced pressure to afford I-48 as a solid, which was used for next step without further purification.

Preparation of Ex. 14:

A solution of I-26 (150 mg, 0.68 mmol), I-48 (240 mg, 0.81 mmol) and DIPEA (260 mg, 2.04 mmol) in NMP (1.0 mL) was heated at 120° C. for 24 h. The reaction mixture was cooled to RT, diluted with EtOAc (30 mL) and washed with brine (3×50 mL). The organic layer was collected, dried over anhydrous Na₂SO₄ and concentrated under reduced pressure. The crude residue was purified by preparative HPLC to afford Ex. 14 (12.0 mg, 4%) as a solid. MS (MM) m/z 480.1 [M+H]⁺.

¹H NMR (300 MHz, DMSO-d₆): δ 8.66 (s, 1H), 8.54 (s, 1H), 7.95 (s, 1H), 7.79 (s, 1H), 6.36 (s, 1H), 3.89 (br d, J=9.3 Hz, 2H), 3.34-3.10 (m, 7H), 3.12 (d, J=11.7 Hz, 1H), 2.22-2.14 (m, 2H), 1.97-1.92 (m, 1H), 1.54 (d, J=11.7 Hz, 1H), 1.29-1.23 (m, 3H), 1.13 (s, 6H).

Example 15: 6,6-Dimethyl-3-phenyl-8-(7-(trifluoromethyl)imidazo[1,5-a]pyridin-5-yl)-1,3,8-triazaspiro[4.5]decane-2,4-dione

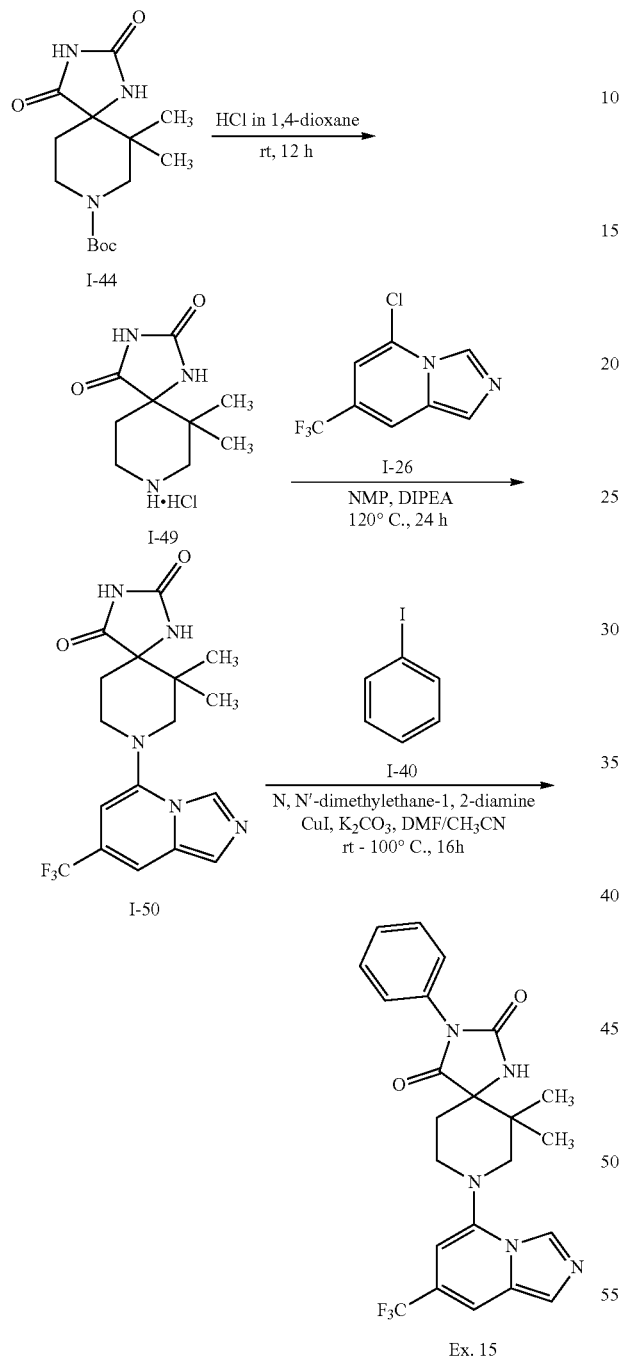

Ex. 15

Preparation of I-49:
A mixture of I-44 (1.00 g, 3.3 mmol) and HCl in 1,4-dioxane (4 M, 15 mL) was stirred at RT for 12 h. The solvent was evaporated under reduced pressure to afford I-49 as a solid.

Preparation of I-50:
A solution of I-26 (200 mg, 0.90 mmol), I-49 (166 mg, 0.99 mmol) and DIPEA (340 mg, 2.7 mmol) in NMP (1.0 mL) was heated at 120° C. for 24 h. The reaction mixture was cooled to RT, diluted with EtOAc (30 mL) and washed with brine (3×50 mL). The organic layer was collected, dried over anhydrous $Na_2SO_4$ and concentrated under reduced pressure to afford I-50 as a solid, which was used for next step without further purification.

Preparation of Ex. 15:
A stirred solution of I-50 (100 mg, 0.26 mmol) in a mixture of acetonitrile (20 mL) and DMF (20 mL) was charged with I-40 (69.0 mg, 0.33 mmol), $K_2CO_3$ (115 mg, 0.84 mmol), N,N'-dimethylethane-1,2-diamine (7.00 mg, 0.08 mmol) and CuI (15.0 mg, 0.08 mmol) at RT. The reaction mixture was heated at 100° C. for 16 h. The reaction mixture was treated with water (15 mL) and extracted with EtOAc (3×20 mL). The combined organic layer was washed with brine (5×20 mL), dried over anhydrous $Na_2SO_4$ and evaporated under reduced pressure. The crude compound was purified on preparative TLC (100% EtOAc) to afford Ex. 15 as a solid. MS (MM) m/z 458.2 $[M+H]^+$.

$^1$H NMR (400 MHz, DMSO-$d_6$): δ 8.81 (s, 1H), 8.45 (s, 1H), 7.83 (s, 1H), 7.67 (s, 1H), 7.44-7.41 (m, 2H), 7.36-7.28 (m, 2H), 6.24 (s, 1H), 3.35-3.32 (m, 1H), 3.20-3.10 (m, 2H), 3.05 (d, J=12.0 Hz, 1H), 2.28-2.25 (m, 1H), 2.20-2.10 (m, 1H), 1.10 (s, 6H).

Example 16: 8-(7-Bromoimidazo[1,5-a]pyridin-5-yl)-6,6-dimethyl-1,3,8-triazaspiro[4.5]decane-2,4-dione

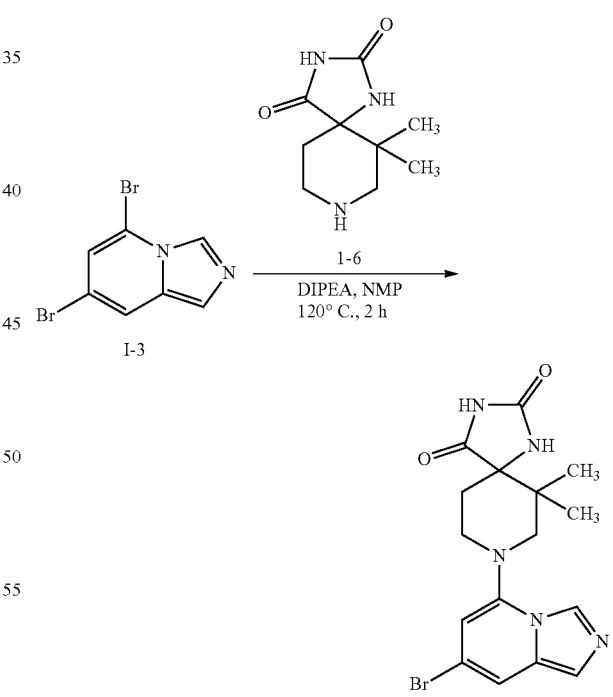

Ex. 16

Preparation of Ex. 16:
A solution of compound I-3 (300 mg, 0.365 mmol), compound I-6 (85.0 mg, 0.434 mmol) and DIPEA (94.0 mg, 0.730 mmol) in NMP (3.0 mL) was irradiated under microwave at 120° C. for 2 h. The reaction mixture was cooled to RT, diluted with EtOAc (50 mL), washed with water (2×50 mL) and brine (20 mL). The organic layer was separated, dried over anhydrous Na$_2$SO$_4$ and concentrated in vacuo. The residue was purified by combiflash column chromatography using Redisep® column (12 g, hexanes/EtOAc, 1:1) to afford the title compound as a solid. MS (MM) m z 392.0 [M+H]$^+$.

$^1$H NMR (300 MHz, DMSO-d$_6$): δ 10.72 (s, 1H), 8.28 (s, 1H), 8.24 (s, 1H), 7.64 (s, 1H), 7.40 (s, 1H), 6.24 (s, 1H), 3.32 (s, 1H), 3.19-3.15 (m, 2H), 2.98 (d, J=10.8 Hz, 1H), 2.08-2.06 (m, 2H), 1.07 (s, 6H).

Chemical structures, names and molecular mass of the compounds in Examples 1-16 are summarized in the following table.

| Ex. # | Structure | Chemical Name | Mass |
|---|---|---|---|
| 1 | 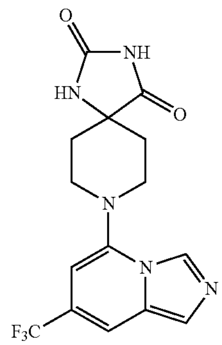 [SMILES: O=C1NC(=O)C2(CCN(c3cc(C(F)(F)F)cc4cncn34)CC2)N1] | 8-(7-(Trifluoromethyl)imidazo[1,5-a]pyridin-5-yl)-1,3,8-triazaspiro[4.5]decane-2,4-dione | 354.1 |
| 2 | 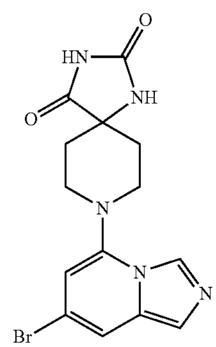 | 8-(7-bromoimidazo[1,5-a]pyridin-5-yl)-1,3,8-triazaspiro[4.5]decane-2,4-dione | 364 |
| 3 | 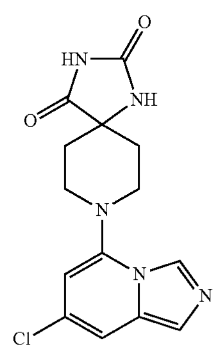 [SMILES: O=C1NC(=O)C2(CCN(c3cc(Cl)cc4cncn34)CC2)N1] | 8-(7-chloroimidazo[1,5-a]pyridin-5-yl)-1,3,8-triazaspiro[4.5]decane-2,4-dione | 320.1 |
| 4 | 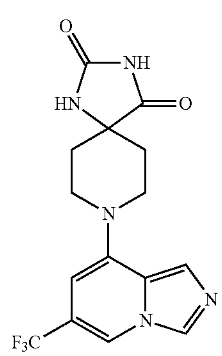 [SMILES: O=C1NC(=O)C2(CCN(c3cc(C(F)(F)F)cn4cncc34)CC2)N1] | 8-(6-(trifluoromethyl)imidazo[1,5-a]pyridin-8-yl)-1,3,8-triazaspiro[4.5]decane-2,4-dione | 354.1 |

| Ex. # | Structure | Chemical Name | Mass |
|---|---|---|---|
| 5 | 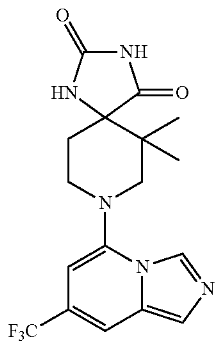 [SMILES: CC1(C)CN(c2cc(C(F)(F)F)cc3cncn23)CCC12NC(=O)NC2=O] | 6,6-dimethyl-8-(7-(trifluoromethyl)imidazo[1,5-a]pyridin-5-yl)-1,3,8-triazaspiro[4.5]decane-2,4-dione | 382.1 |
| 6 | 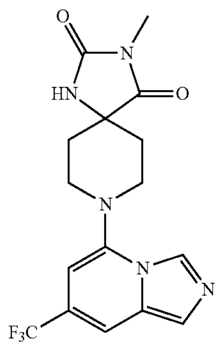 [SMILES: CN1C(=O)NC2(CCN(c3cc(C(F)(F)F)cc4cncn34)CC2)C1=O] | 3-methyl-8-(7-(trifluoromethyl)imidazo[1,5-a]pyridin-5-yl)-1,3,8-triazaspiro[4.5]decane-2,4-dione | 368.1 |
| 7 | 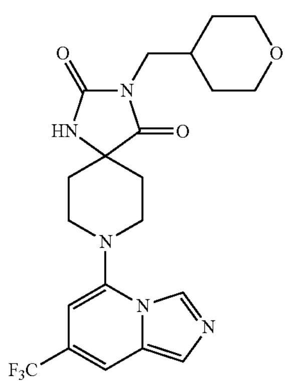 [SMILES: O=C1NC2(CCN(c3cc(C(F)(F)F)cc4cncn34)CC2)C(=O)N1CC1CCOCC1] | 3-((tetrahydro-2H-pyran-4-yl)methyl)-8-(7-(trifluoromethyl)imidazo[1,5-a]pyridin-5-yl)-1,3,8-triazaspiro[4.5]decane-2,4-dione | 452.1 |
| 8 | 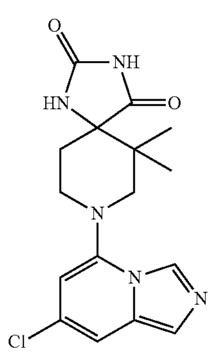 [SMILES: CC1(C)CN(c2cc(Cl)cc3cncn23)CCC12NC(=O)NC2=O] | 8-(7-chloroimidazo[1,5-a]pyridin-5-yl)-6,6-dimethyl-1,3,8-triazaspiro[4.5]decane-2,4-dione | 346.1 |

| Ex. # | Structure | Chemical Name | Mass |
|---|---|---|---|
| 9 | 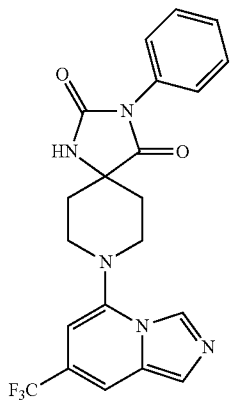 [SMILES: O=C1NC2(CCN(c3cc(C(F)(F)F)cc4cncn34)CC2)C(=O)N1c1ccccc1] | 3-phenyl-8-(7-(trifluoromethyl)imidazo[1,5-a]pyridin-5-yl)-1,3,8-triazaspiro[4.5]decane-2,4-dione | 430.1 |
| 10 | 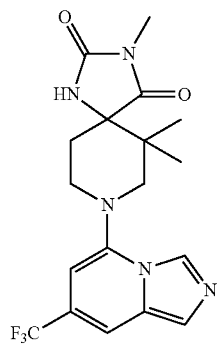 [SMILES: CN1C(=O)NC2(CCN(c3cc(C(F)(F)F)cc4cncn34)CC2(C)C)C1=O] | 3,6,6-trimethyl-8-(7-(trifluoromethyl)imidazo[1,5-a]pyridin-5-yl)-1,3,8-triazaspiro[4.5]decane-2,4-dione | 396.1 |
| 11 | 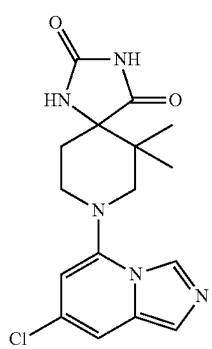 [SMILES: CC1(C)CN(c2cc(Cl)cc3cncn23)CCC12NC(=O)NC2=O] | 8-(7-chloroimidazo[1,5-a]pyridin-5-yl)-6,6-dimethyl-1,3,8-triazaspiro[4.5]decane-2,4-dione | 348.1 |
| 12 | 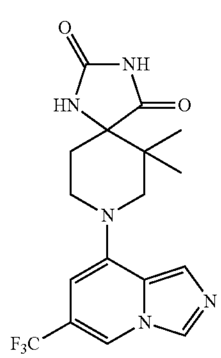 [SMILES: CC1(C)CN(c2cc(C(F)(F)F)cn3cncc23)CCC12NC(=O)NC2=O] | 6,6-dimethyl-8-(6-(trifluoromethyl)imidazo[1,5-a]pyridin-8-yl)-1,3,8-triazaspiro[4.5]decane-2,4-dione | 382.1 |

-continued

| Ex. # | Structure | Chemical Name | Mass |
|---|---|---|---|
| 13 | 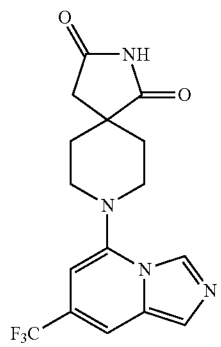 [SMILES: O=C1CC2(CCN(c3cc(C(F)(F)F)cc4cncn34)CC2)C(=O)N1] | 8-(7-(trifluoromethyl)imidazo[1,5-a]pyridin-5-yl)-2,8-diazaspiro[4.5]decane-1,3-dione | 353 |
| 14 | 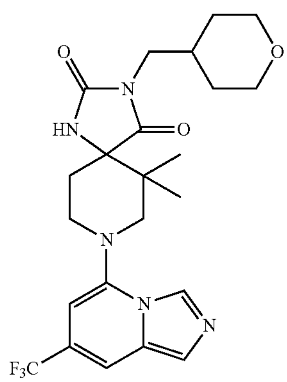 [SMILES: CC1(C)CN(c2cc(C(F)(F)F)cc3cncn23)CCC12NC(=O)N(CC1CCOCC1)C2=O] | 6,6-dimethyl-3-((tetrahydro-2H-pyran-4-yl)methyl)-8-(7-(trifluoromethyl)imidazo[1,5-a]pyridin-5-yl)-1,3,8-triazaspiro[4.5]decane-2,4-dione | 480.1 |
| 15 | 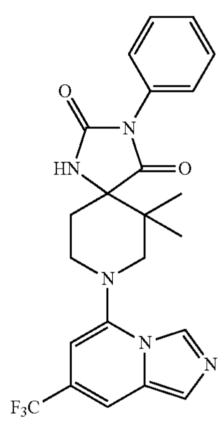 [SMILES: CC1(C)CN(c2cc(C(F)(F)F)cc3cncn23)CCC12NC(=O)N(c1ccccc1)C2=O] | 6,6-dimethyl-3-phenyl-8-(7-(trifluoromethyl)imidazo[1,5-a]pyridin-5-yl)-1,3,8-triazaspiro[4.5]decane-2,4-dione | 458.2 |
| 16 | 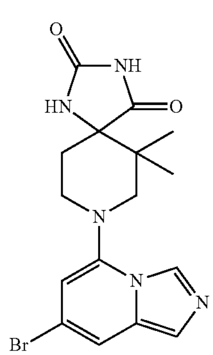 [SMILES: CC1(C)CN(c2cc(Br)cc3cncn23)CCC12NC(=O)NC2=O] | 8-(7-bromoimidazo[1,5-a]pyridin-5-yl)-6,6-dimethyl-1,3,8-triazaspiro[4.5]decane-2,4-dione | 392 |

Example 17: 8-(7-(trifluoromethyl)imidazo[1,5-a]pyridin-5-yl)-2-oxa-8-azaspiro[4.5]decan-1-one

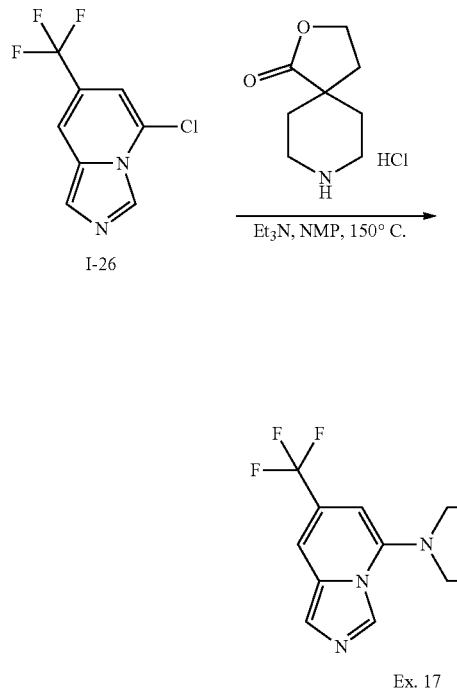

Ex. 17

To a vial were added 5-chloro-7-(trifluoromethyl)imidazo[1,5-a]pyridine (I-26) (22 mg, 0.10 mmol), 2-oxa-8-azaspiro[4.5]decan-1-one hydrochloride (commerically available from Enamine Building Blocks) (38 mg, 0.20 mmol), NMP (300 ul) and Et$_3$N (100 ul, 0.72 mmol). The resulting mixture was stirred at 150° C. for 20 h. The mixture was filtered and purified on reversed phase, preparative HPLC (15%-70% ACN in water with 0.1% NH$_4$OH) to afford 8-(7-(trifluoromethyl)imidazo[1,5-a]pyridin-5-yl)-2-oxa-8-azaspiro[4.5]decan-1-one (Ex. 17). [M+H]$^+$ 340.

$^1$H NMR (500 MHz, DMSO-d6) δ 8.44 (s, 1H), 7.88 (s, 1H), 7.72 (s, 1H), 6.32 (s, 1H), 4.40-4.30 (m, 2H), 3.50-3.25 (m, 2H), 2.99 (t, J=10 Hz, 1H), 2.60-2.40 (m, 1H), 2.35-2.25 (m, 2H), 2.10-1.95 (m, 2H), 1.85-1.75 (m, 2H); MS (EI) Calc'd for C$_{16}$H$_{17}$F$_3$N$_3$O$_2$

Example 18 this compound was synthesized in an analogous fashion to Ex. 17, except that 2-methyl-1,3,8-triazaspiro[4.5]dec-1-en-4-one (commerically available from Ark Pharm, Inc.) was used in place of 2-oxa-8-azaspiro[4.5]decan-1-one hydrochloride.

Example 19 this compound was synthesized in an analogous fashion to Ex. 17, expect that 2,8-diazaspiro[4.5]decan-1-one hydrochloride (commerically available from Ark Pharm, Inc.) was used in place of 2-oxa-8-azaspiro[4.5]decan-1-one hydrochloride.

Example 20: 1-(9-(7-(Trifluoromethyl)imidazo[1,5-a]pyridin-5-yl)-3,9-diazaspiro[5.5]undecan-3-yl)ethan-1-one

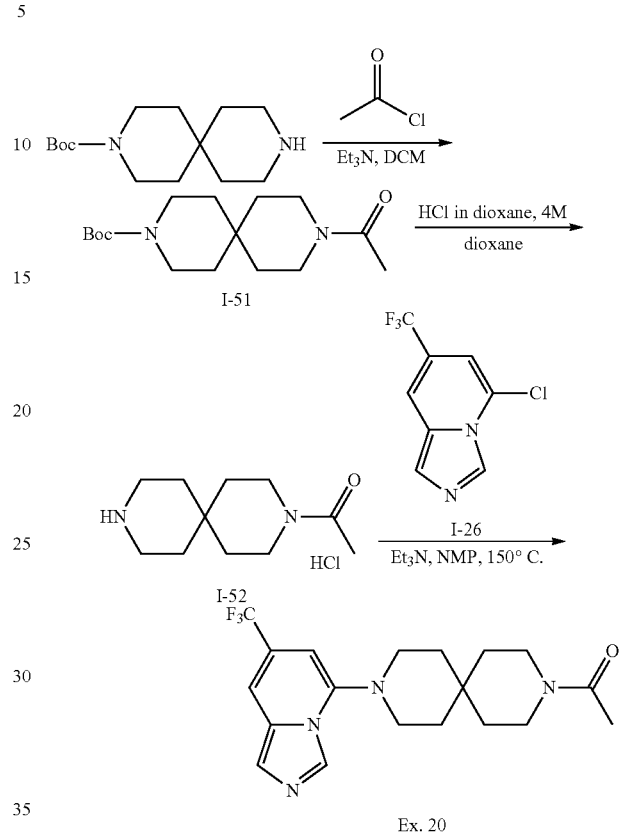

Ex. 20

Tert-butyl 3,9-diazaspiro[5.5]undecane-3-carboxylate (commercially available from Ark Pharm, Inc.) (100 mg, 0.40 mmol) was dissolved in DCM (1 ml), and TEA (200 ul, 1.4 mmol) was added. The solution was cooled to 0° C., after which acetyl chloride (31 mg, 0.4 mmol) was added dropwise as a solution in DCM (0.1 ml). The resulting mixture was allowed to come to RT and was stirred for 18 h. The solvent was then removed in vacuo to provide tert-butyl 9-acetyl-3,9-diazaspiro[5.5]undecane-3-carboxylate (I-51), which was used without further purification. Tert-butyl 9-acetyl-3,9-diazaspiro[5.5]undecane-3-carboxylate (I-51) was then dissolved in dioxane (1 ml) and HCl in dioxane (4M, 1 ml, 4.0 mmol) was added. The mixture was allowed to stir at RT for 18 h, after which the solvent was removed in vacuo to afford 1-(3,9-diazaspiro[5.5]undecan-3-yl)ethan-1-one hydrochloride (I-52), which was used without further purification. 1-(3,9-Diazaspiro[5.5]undecan-3-yl)ethan-1-one hydrochloride (I-52) was then dissolved in NMP (1 ml), after which 5-chloro-7-(trifluoromethyl)imidazo[1,5-a]pyridine (I-26) (25 mg, 0.11 mmol) and Et$_3$N (800 ul, 5.7 mmol) were added. The mixture was heated to 150° C. and was stirred for 20 h. The mixture was then filtered, and purified directly via reverse-phase, mass-triggered HPLC (10%-100% ACN in water with 0.1% TFA) to afford 1-(9-(7-(trifluoromethyl)imidazo[1,5-a]pyridin-5-yl)-3,9-diazaspiro[5.5]undecan-3-yl)ethan-1-one (Ex. 20). MS (EI) Calc'd for C$_{19}$H$_{24}$F$_3$N$_4$O [M+H]$^+$ 381.

$^1$H NMR (500 MHz, DMSO-d6) δ 8.59 (s, 1H), 7.91 (s, 1H), 7.83 (s, 1H), 6.41 (s, 1H), 3.30-3.00 (m, 4H), 2.65-2.30 (m, 4H), 2.01 (s, 3H), 1.85-1.65 (m, 4H), 1.65-1.40 (m, 4H)

Chemical structures, names and molecular mass of the compounds in Examples 17-20 are summarized in the following table.

| Ex. # | Structure | Chemical Name | Mass |
|---|---|---|---|
| 17 | 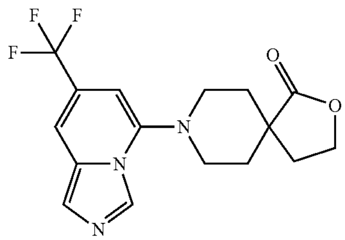 [SMILES: O=C1OCCC12CCN(c1cc(C(F)(F)F)cc3cncn13)CC2] | 8-(7-(trifluoromethyl)imidazo[1,5-a]pyridin-5-yl)-2-oxa-8-azaspiro[4.5]decan-1-one | 340 |
| 18 | 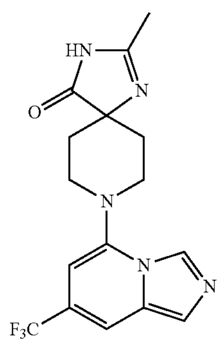 [SMILES: CC1=NC2(CCN(c3cc(C(F)(F)F)cc4cncn34)CC2)C(=O)N1] | 2-methyl-8-(7-(trifluoromethyl)imidazo[1,5-a]pyridin-5-yl)-1,3,8-triazaspiro[4.5]dec-1-en-4-one | 352 |
| 19 | 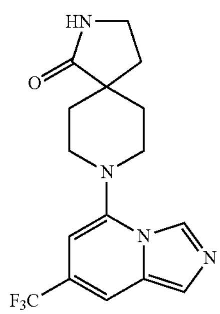 [SMILES: O=C1NCCC12CCN(c1cc(C(F)(F)F)cc3cncn13)CC2] | 8-(7-(trifluoromethyl)imidazo[1,5-a]pyridin-5-yl)-2,8-diazaspiro[4.5]decan-1-one | 339 |
| 20 | 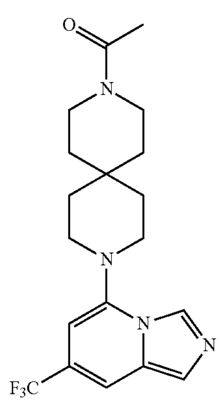 [SMILES: CC(=O)N1CCC2(CC1)CCN(c1cc(C(F)(F)F)cc3cncn13)CC2] | 3-acetyl-9-[7-(trifluoromethyl)imidazo[1,5-a]pyridin-5-yl]-3,9-diazaspiro[5.5]undecane | 381 |

Biological Assays

Exemplary compounds disclosed herein were prepared, and tested to determine their effect as IDO and/or TDO inhibitors. Two different assays were employed: 1. a cell-based assay for detecting the effect of test compounds on kynurenine production in two different cancer cell types. This assay utilized cancer cells which expressed either TDO or IDO and as such was used as a means of testing compound activity at these two enzymes in a cell-based context. 2. a TDO and IDO biochemical coupled assay which utilized recombinantly produced and purified TDO and IDO enzymes in combination with the enzyme formamidase. This coupled enzyme system allowed conversion of N-formylkynurenine produced by TDO or IDO activity to kynurenine which was then quantified by fluorescence following addition of Erhlich's Reagent. The protocols for these are set out below.

A172 and SKOV3 Cell Based Assays for Detection of Kynurenine Produced by TDO and/or IDO A172 (human glioblastoma) and SKOV3 (human ovarian adenocarcinoma) cells were seeded in a 96 well plate at 30,000 or 40,000 cells per well respectively in phenol red-free RPMI supplemented with 10% FCS, 2 mM L-glutamine and 500 µM L-tryptophan. IDO expression was induced in the SKOV3 cells by the addition of 500 ng/ml IFN-γ. Cells were incubated at 37° C. with or without the addition of test compound. After 48 hours, the cells were removed by centrifugation and Erhlich's reagent was added to the supernatant. The Erhlich's reagent was incubated for 5 minutes before the absorbance was read at 490 nM.

TDO and IDO Biochemical Coupled Assay

Recombinant human IDO or TDO was incubated in 50 mM KPO4 (pH 7.0), 0.5 mM EGTA, 0.5 mM EDTA, 0.05% Triton™ X100, 20 mM ascorbate, 10 µM methylene blue, 500 U/ml catalase, 50 µg/ml KynB (kynurenine formamidase). TDO assays were carried out in the presence of 330 µM L-tryptophan, while IDO assays had the addition of 45 µM L-tryptophan. After incubation for 17 minutes at room temperature the reactions were stopped by the addition of Erhlich's reagent and incubated at room temperature for 5 minutes before the fluorescence was read.

The pIC50 values for a variety of test compounds are shown in the following table.

| Ex. No. | pIC50 SKOV3 (IDO) cell based assay | pIC50 A172 (TDO) cell based assay | pIC50 hIDO biochemical coupled assay | pIC50 hTDO biochemical coupled assay |
|---|---|---|---|---|
| 1 | 6.21 | <5 | 7.53 | 5.6 |
| 2 | 6.25 | <5 | 7.19 | 6.29 |
| 3 | 5.85 | <5 | 6.55 | 5.85 |
| 4 | 5.32 | <5 | 5.99 | 5.84 |
| 5 | 6.43 | <5 | 5.92 | 5.52 |
| 6 | 5.21 | <5 | 5.89 | 5.74 |
| 7 | 5.44 | 5 | 5.92 | 5.4 |
| 8 | 6.7 | 5.1 | 6.83 | 5.8 |
| 9 | 5.76 | <5 | 6.58 | 5.78 |
| 10 | 5.11 | <5 | 6.2 | 5.57 |
| 11 | 5.43 | 5.68 | 6.99 | 6.33 |
| 12 | 5.93 | 6.18 | 5.74 | 6.1 |
| 13 | 5.9 | <5 | 6.53 | 5.77 |
| 14 | 5.33 | <5 | 5.92 | 4.78 |
| 15 | 5.25 | <5 | 5.66 | 4.42 |
| 16 | 6.87 | 5.1 | 7.06 | 5.92 |

In addition to the above assays, the activities of certain exemplary compounds were determined using the following IDO1 enzyme and IDO1 cellular assays.

IDO1 Enzyme Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

HIS-tagged IDO1 protein was recombinantly expressed in *Escherichia coli* using ZYP5052 autoinduction media supplemented with 500 µM delta aminolevulinic acid for 48 hours at 16 degrees Celcius. IDO1 protein was purified using $Ni^{2+}$-affinity resin and size exclusion chromatography. Purified protein was then diluted in assay buffer (50 mM Tris pH 7.0, 1% glycerol, 20 µM methylene blue, 0.05% Tween-20, 20 mM sodium ascorbate, 100 units/mL catalase to obtain a final IDO1 concentration of 40 nM. IDO1 solution (30 µM) or buffer alone (30 µM) were dispensed to wells of the assay plate using a BioRAPTR liquid dispenser (Beckman Coulter). Assay plates containing compound and IDO1 enzyme were incubated at room temperature for 30 minutes. Afterwards, 10 µL of 400 µM tryptophan in assay buffer were added to each well of the assay plate using a Bio-RAPTR liquid dispenser. Plates were incubated at room temperature for 60 minutes and reactions were quenched by addition of 10 µL of 0.5 M methyl isonipecotate in dimethyl sulfoxide. Plates were sealed and incubated at 37 degrees Celcius for 4 hours or 50 degrees Celcius for 2 hours. The plates are allowed to cool and then centrifuged for 1 minute at 1000×g. The resulting fluorence was measured in an Envision plate reader (Perkin Elmer) with a 400/25 nm excitation filter and an 510/20 nm emission filter.

The fluoresence intensity of each well was corrected for the background observed in wells that did not receive IDO1 and was expressed as a fraction of the intensity observed in wells that received IDO1 enzyme and DMSO only. Potencies were calculated by linear least squares fit to the four parameter logistic IC50 equation.

IDO1 HEK293 Cellular Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 550 acoustic liquid handler (Labcyte).

HEK293 cell pellets were resuspended to $5 \times 10^5$ cells/mL in complete HEK293 culture media (89% DMEM, 10% FBS, 1% penicilllin/streptomycin). Suspended cells (2 mL) were dispensed into each well of a 6-well Corning plate (Catalog #3516). Cells were allowed to attach and were incubated for 20 hours at 37 degrees Celcius in a 5% $CO_2$ incubator. Flag-IDO1 vector (Genscript True ORF Gold, 2 ug) in 150 uL of Opti-MEM medium was added to to each well of a Corning 24 well plate (Cat #3527) and incubated for 5 minutes at room temperature. To each well of the 24-well plate was added 150 µL Lipofectamine 2000 (Gibco) and the plate incubated at room temperature for 20-30 minutes. To each well of attached cells in the 6-well plate, 250 µL of the transfection mix from the 24-well plate was gently added to each well and IDO1 protein was allowed to express for 24-30 hours at 37 degrees Celcius in a 5% $CO_2$ incubator.

Media was removed from the cells which were then washed with 2 mL Dulbecco's phosphate-buffered saline (DPBS). After removal of DPBS, 0.5 mL of TrypLE (Gibco) was added and incubated at 5 minutes until cells lift from the surface of the wells. Complete HEK293 culture media (4 mL) was added to each well and cells were collected and pooled into a conical tube. Cells were pelleted at 200×g for 5 minutes and resuspended in an equal volume of complete DMEM medium. Cells were diluted to $4 \times 10^5$ cells per mL in complete HEK293 media. L-Tryptophan was added to added to give a final concentration of 200 µM. The diluted transfected cells (50 µL) or nontransfected cells (50 µL) were dispensed into wells of Greiner black 384-well assay plates (catalog #781086) containing previously diluted compounds. The plate is briefly mixed and centrifuged at 200×g for 10 seconds to collect cells at the bottom of the plate. Plates were covered and incubated for 20-24 hours at 37 degrees C. in a 5% $CO_2$ incubator. Afterwards 10 µL of 0.5 M methyl isonipecotate in dimethyl sulfoxide was added to each well, mixed, sealed, and centrifuged at 500 rpm for 10 seconds. Plates were incubated at 37 degrees in a 5% $CO_2$ incubator overnight to develop fluoresence. The plates are allowed to cool and then centrifuged for 1 minute at 1000×g.

The resulting fluoresence was measured in an Envision plate reader (Perkin Elmer) with a 400/25 nm excitation filter and an 510/20 nm emission filter.

The fluoresence intensity of each well was corrected for the background observed in wells with untransfected cells and was expressed as a fraction of the intensity observed in wells of IDO1 transfected cells and DMSO only. Potencies were calculated by linear least squares fit to the four parameter logistic $IC_{50}$ equation.

The pIC50 values for a variety of test compounds are shown in the following table.

| Ex. No. | IDO1 Enzyme Assay, $pIC_{50}$ | HEK293 Cell Assay, $pIC_{50}$ |
|---|---|---|
| 17 | 5.7 | 5.8 |
| 18 | 5.7 | 5.8 |
| 19 | 5.1 | 5.2 |
| 20 | 5.2 | 5.7 |

As can be seen from the above activity data, compounds disclosed herein are inhibitors of the IDO and/or TDO enzymes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

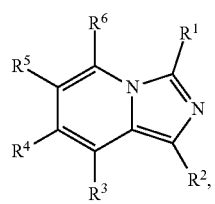

(I)

wherein:
each of $R^1$ and $R^2$ is independently selected from the group consisting of (1) H and (2) $NH_2$;
one of $R^3$ and $R^6$ is H and the other is $Y^1$;
each of $R^4$ and $R^5$ is independently selected from the group consisting of (1) H, (2) halogen, (3) $C_{1-6}$ alkyl, optionally substituted with one to three halogens, (4) $C_{3-6}$ cycloalkyl, (5) $C_{1-6}$ alkoxy, optionally substituted with one to three halogens, (6) CN, and (7) $-NR^gR^{g'}$, each of $R^g$ and $R^{g'}$ is independently selected from the group consisting of H, $C_{1-6}$ alkyl, $-COH$, and $-COC_{1-6}$ alkyl;

$Y^1$ is a group having the following formula:

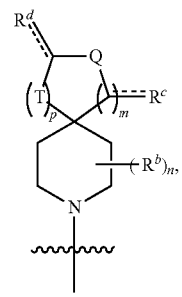

dashed line "- - - - -" represents an optional double bond;
Q is $-C(R^a)(R^{a'})-$, $-N(R^a)-$, or $-O-$;
T is $-C(R^a)(R^{a'})-$, $-N(R^a)-$, or $-O-$;
$R^a$ is selected from the group consisting of (1) H, (2) $C_{1-10}$ alkyl, (3) aryl, (4) $-C(O)-R^e$, (5) $-SO_2-NH_2$, and (6) $-SO_2-C_{1-4}$ alkyl; wherein each of the alkyl and aryl is optionally substituted with one to three substituents independently selected from halogen and heterocyclyl;
$R^{a'}$ is selected from the group consisting of (1) H and (2) $C_{1-6}$ alkyl;
$R^b$ is $C_{1-6}$ alkyl;
each of $R^c$ and $R^d$ is independently selected from the group consisting of (1) H, (2) $C_{1-6}$ alkyl and (3) oxo;
$R^e$ is selected from the group consisting of (1) $C_{1-6}$ alkyl, (2) aryl and (3) heteroaryl;
m is 0, 1 or 2;
n is 0, 1 or 2; and
p is 0 or 1.

2. The compound of claim 1, or a pharmaceutically acceptable salt thereof, wherein each of $R^1$ and $R^2$ is H.

3. The compound of claim 1, or a pharmaceutically acceptable salt thereof, wherein each of $R^4$ and $R^5$ is independently selected from the group consisting of (1) H, (2) halogen, (3) $C_{1-4}$ alkyl, optionally substituted with one to three halogens.

4. The compound of claim 1, or a pharmaceutically acceptable salt thereof, wherein each of $R^4$ and $R^5$ is independently selected from the group consisting of (1) H, (2) halogen, (3) $-CF_3$; and m is 1.

5. The compound of claim 1, or a pharmaceutically acceptable salt thereof, wherein:
$R^3$ is H;
$R^6$ is $Y^2$ having the following formula:

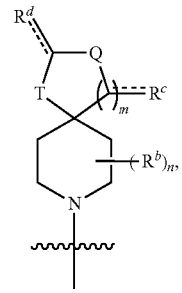

wherein
dashed line "- - - - -" represents an optional double bond;
Q is $-CH(R^a)-$ or $-N(R^a)-$;
T is $-CH_2-$ or $-NH-$;

R$^a$ is selected from the group consisting of (1) H, (2) C$_{1-6}$ alkyl, and (3) phenyl; wherein each of the alkyl and phenyl is optionally substituted with one to three substituents independently selected from halogen and a 5- or 6-membered hetero monocyclic group containing one hetero ring atom selected from oxygen, sulfur and nitrogen;

R$^b$ is C$_{1-4}$ alkyl;

each of R$^c$ and R$^d$ is independently H or oxo; and m is 1.

6. The compound of claim 1, or a pharmaceutically acceptable salt thereof, wherein:

R$^3$ is H;

R$^6$ is Y$^3$ having the following formula:

[structure]

wherein

Q is —N(R$^a$)—;

T is —CH$_2$— or —NH—;

R$^a$ is selected from the group consisting of (1) H, (2) C$_{1-6}$ alkyl, optionally substituted with one to three substituents independently selected from halogen and a 5- or 6-membered hetero monocyclic group containing one oxygen ring atom, and (3) phenyl;

R$^b$ is methyl or ethyl; and n is 0, 1 or 2.

7. The compound of claim 1, or a pharmaceutically acceptable salt thereof, wherein Y$^1$ is selected from the group consisting of:

[structures]

8. The compound of claim 1 having formula (Ia), or a pharmaceutically acceptable salt thereof:

(Ia)

[structure]

wherein:

R$^4$ is selected from the group consisting of (1) halogen and (2) C$_{1-4}$ alkyl, optionally substituted with one to three halogens;

R$^6$ is Y$^2$ having the following formula:

[structure]

wherein dashed line " ------ " represents an optional double bond;

Q is —CH(R$^a$)— or —N(R$^a$)—;

T is —CH$_2$— or —NH—;

R$^a$ is selected from the group consisting of (1) H, (2) C$_{1-4}$ alkyl, and (3) phenyl; wherein each of the alkyl and phenyl is optionally substituted with one to three substituents independently selected from halogen and heterocyclyl;

R$^b$ is C$_{1-4}$ alkyl;

each of R$^c$ and R$^d$ is independently H or oxo;

m is 1; and n is 0, 1 or 2.

9. The compound of claim 8, or a pharmaceutically acceptable salt thereof, wherein $R^6$ is $Y^3$ having the following formula:

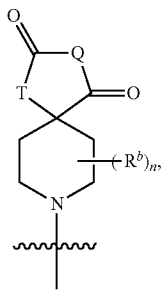

wherein

Q is —N($R^a$)—;

T is —CH$_2$— or —NH—;

$R^a$ is selected from the group consisting of (1) H, (2) C$_{1-4}$ alkyl, optionally substituted with one to three substituents independently selected from halogen and tetrahydropyranyl, and (3) phenyl; and $R^b$ is methyl.

10. The compound of claim 1 having formula (Ib), or a pharmaceutically acceptable salt thereof:

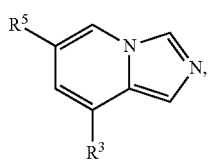 (Ib)

$R^5$ is selected from the group consisting of (1) halogen and (2) C$_{1-4}$ alkyl, optionally substituted with one to three halogens;

$R^3$ is $Y^2$ having the following formula:

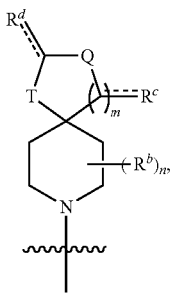

wherein dashed line " ------ " represents an optional double bond;

Q is —CH($R^a$)— or —N($R^a$)—;

T is —CH$_2$— or —NH—;

$R^a$ is selected from the group consisting of (1) H, (2) C$_{1-6}$ alkyl, and (3) phenyl; wherein each of the alkyl and phenyl is optionally substituted with one to three substituents independently selected from halogen and heterocyclyl;

$R^b$ is C$_{1-4}$ alkyl;

each of $R^c$ and $R^d$ is independently H or oxo;

m is 1; and n is 0, 1 or 2.

11. The compound of claim 10, or a pharmaceutically acceptable salt thereof, wherein $R^3$ is $Y^3$ having the following formula:

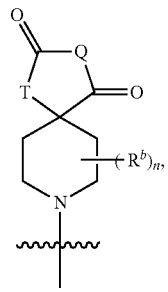

wherein

Q is —N($R^a$)—;

T is —CH$_2$— or —NH—;

$R^a$ is selected from the group consisting of (1) H, (2) C$_{1-4}$ alkyl, optionally substituted with one to three substituents independently selected from halogen and tetrahydropyranyl, and (3) phenyl; and $R^b$ is methyl.

12. The compound of claim 1 selected from the group consisting of:

8-(7-(Trifluoromethyl)imidazo[1,5-a]pyridin-5-yl)-1,3,8-triazaspiro[4.5]decane-2,4-dione, 8-(7-bromoimidazo[1,5-a]pyridin-5-yl)-1,3,8-triazaspiro[4.5]decane-2,4-dione, 8-(7-chloroimidazo[1,5-a]pyridin-5-yl)-1,3,8-triazaspiro[4.5]decane-2,4-dione, 8-(6-(trifluoromethyl)imidazo[1,5-a]pyridin-8-yl)-1,3,8-triazaspiro[4.5]decane-2,4-dione, 6,6-dimethyl-8-(7-(trifluoromethyl)imidazo[1,5-a]pyridin-5-yl)-1,3,8-triazaspiro[4.5]decane-2,4-dione, 3-methyl-8-(7-(trifluoromethyl)imidazo[1,5-a]pyridin-5-yl)-1,3,8-triazaspiro[4.5]decane-2,4-dione, 3-((tetrahydro-2H-pyran-4-yl)methyl)-8-(7-(trifluoromethyl)imidazo[1,5-a]pyridin-5-yl)-1,3,8-triazaspiro[4.5]decane-2,4-dione, 8-(7-chloroimidazo[1,5-a]pyridin-5-yl)-6,6-dimethyl-1,3,8-triazaspiro[4.5]decane-2,4-dione, 3-phenyl-8-(7-(trifluoromethyl)imidazo[1,5-a]pyridin-5-yl)-1,3,8-triazaspiro[4.5]decane-2,4-dione, 3,6,6-trimethyl-8-(7-(trifluoromethyl)imidazo[1,5-a]pyridin-5-yl)-1,3,8-triazaspiro[4.5]decane-2,4-dione, 8-(7-chloroimidazo[1,5-a]pyridin-5-yl)-6,6-dimethyl-1,3,8-triazaspiro[4.5]decane-2,4-dione, 6,6-dimethyl-8-(6-(trifluoromethyl)imidazo[1,5-a]pyridin-8-yl)-1,3,8-triazaspiro[4.5]decane-2,4-dione, 8-(7-(trifluoromethyl)imidazo[1,5-a]pyridin-5-yl)-2,8-diazaspiro[4.5]decane-1,3-dione, 6,6-dimethyl-3-((tetrahydro-2H-pyran-4-yl)methyl)-8-(7-(trifluoromethyl)imidazo[1,5-a]pyridin-5-yl)-1,3,8-triazaspiro[4.5]decane-2,4-dione, 6,6-dimethyl-3-phenyl-8-(7-(trifluoromethyl)imidazo[1,5-a]pyridin-5-yl)-1,3,8-triazaspiro[4.5]decane-2,4-dione, 8-(7-bromoimidazo[1,5-a]pyridin-5-yl)-6,6-dimethyl-1,3,8-triazaspiro[4.5]decane-2,4-dione, 8-(7-bromoimidazo[1,5-a]pyridin-5-yl)-6,6-dimethyl-1,3,8-triazaspiro[4.5]decane-2,4-dione, 8-(7-(trifluoromethyl)imidazo[1,5-a]pyridin-5-yl)-2-oxa-8-azaspiro[4.5]decan-1-one, 2-methyl-8-(7-(trifluoromethyl)imidazo[1,5-a]pyridin-5-yl)-1,3,8-triazaspiro[4.5]dec-1-en-4-one, 1-(9-(7-(trifluoromethyl)imidazo[1,5-a]pyridin-5-yl)-3,9-diazaspiro[5.5]undecan-3-yl)ethan-1-one, and 8-(7-(trifluoromethyl)imidazo[1,5-a]pyridin-5-yl)-2,8-diazaspiro[4.5]decan-1-one;

or a pharmaceutically acceptable salt thereof.

13. A composition comprising a compound of claim 1 or a pharmaceutically acceptable salt thereof, and a pharmaceutically acceptable carrier.

14. A method for treating an IDO- and/or TDO-associated disease or disorder in a mammalian subject which comprises administering to the subject an effective amount of a compound of claim 1 or a pharmaceutically acceptable salt thereof, wherein the disease or disorder is a cancer selected from human glioblastoma and human ovarian adenocarcinoma.

* * * * *

UNITED STATES PATENT AND TRADEMARK OFFICE
CERTIFICATE OF CORRECTION

PATENT NO. : 11,096,930 B2  
APPLICATION NO. : 16/088873  
DATED : August 24, 2021  
INVENTOR(S) : Phillip M. Cowley et al.

Page 1 of 1

It is certified that error appears in the above-identified patent and that said Letters Patent is hereby corrected as shown below:

On the Title Page

Item (71), should read:  
(71) Applicants: IOMet Pharma Ltd., Edinburgh (UK)  
                Merck Sharp & Dohme Corp. (US)

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*